United States Patent
Okada et al.

(10) Patent No.: US 11,773,512 B2
(45) Date of Patent: *Oct. 3, 2023

(54) FIBER DEPOSIT PRODUCTION METHOD, MEMBRANE PRODUCTION METHOD, AND MEMBRANE ADHESION METHOD

(71) Applicant: Kao Corporation, Tokyo (JP)

(72) Inventors: Tomonari Okada, Tsukuba (JP);
Masayuki Uchiyama, Chiba (JP);
Naomi Amari, Ichikai-machi (JP);
Yuko Wakahara, Narashino (JP);
Takehiko Tojo, Utsunomiya (JP);
Hideo Kobayashi, Koto-ku (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/772,472

(22) PCT Filed: Oct. 26, 2020

(86) PCT No.: PCT/JP2020/040153
§ 371 (c)(1),
(2) Date: Apr. 27, 2022

(87) PCT Pub. No.: WO2021/085394
PCT Pub. Date: May 6, 2021

(65) Prior Publication Data
US 2022/0372658 A1 Nov. 24, 2022

(30) Foreign Application Priority Data

Oct. 28, 2019 (JP) .................................. 2019-195659
Oct. 28, 2019 (JP) .................................. 2019-195709

(51) Int. Cl.
*D01D 5/00* (2006.01)
*D01D 5/04* (2006.01)
(Continued)

(52) U.S. Cl.
CPC ........... *D01D 5/0015* (2013.01); *A45D 44/22* (2013.01); *A61Q 19/00* (2013.01); *D01D 5/0076* (2013.01);
(Continued)

(58) Field of Classification Search
CPC .. D01D 5/0046; D01D 5/0061; D01D 5/0076; D01D 7/00; D01D 5/0015
See application file for complete search history.

(56) References Cited

U.S. PATENT DOCUMENTS 5,248,455 A * 9/1993 Joseph ................. D01D 5/0985
264/119
5,945,111 A * 8/1999 Esser .................... B05B 5/1608
424/47

(Continued)

FOREIGN PATENT DOCUMENTS

| CN | 102776583 A | 11/2012 |
|---|---|---|
| CN | 105073091 A | 11/2015 |

(Continued)

OTHER PUBLICATIONS

U.S. Appl. No. 17/772,480, filed Apr. 27, 2022, Naomi Amari, et al.
(Continued)

*Primary Examiner* — Emmanuel S Luk
(74) *Attorney, Agent, or Firm* — Oblon, McClelland, Maier & Neustadt, L.L.P.

(57) ABSTRACT

A fiber collection tool for collecting a fiber spun by electrospinning is described. The fiber collection tool has a size holdable by the hand of a user, and includes, in its interior, an electroconductive section. Preferably, the fiber collection tool further includes a surface section outside the electroconductive section. In a fiber deposit production method, a user collects, with the fiber collection tool, a fiber spun by the user by performing electrospinning using an electrospin-
(Continued)

ning device having a size holdable by the hand of the user, and thereby produces a film including a deposit of the fiber on a surface of the fiber collection tool. The fiber collection tool, having the deposit formed thereon, is pressed against a surface of an object, and the deposit is transferred onto the surface of the object, to form a film including the fiber deposit on the surface of the object.

14 Claims, 4 Drawing Sheets

(51) Int. Cl.
  *D01D 7/00* (2006.01)
  *D04H 1/728* (2012.01)
  *A61Q 19/00* (2006.01)
  *A45D 44/22* (2006.01)
(52) U.S. Cl.
  CPC ............. *D01D 5/0092* (2013.01); *D01D 5/04* (2013.01); *D01D 7/00* (2013.01); *D04H 1/728* (2013.01); *A61K 2800/87* (2013.01)

(56) References Cited

U.S. PATENT DOCUMENTS

| | | | |
|---|---|---|---|
| 6,074,869 A * | 6/2000 | Pall | B01D 61/18 422/429 |
| 6,135,369 A * | 10/2000 | Prendergast | B05B 5/0531 239/690 |
| 6,311,903 B1 * | 11/2001 | Gaw | A45D 34/00 239/708 |
| 6,514,504 B1 * | 2/2003 | Yen | A61K 8/8152 424/490 |
| 6,531,142 B1 * | 3/2003 | Rabe | A61K 8/29 424/490 |
| 7,105,058 B1 * | 9/2006 | Sinyagin | B05B 5/1691 118/62 |
| 9,871,240 B2 * | 1/2018 | Orilall | H01M 50/403 |
| 11,161,126 B2 * | 11/2021 | Tojo | A61Q 1/02 |
| 2002/0102897 A1 * | 8/2002 | Berrigan | D01D 5/0985 156/244.19 |
| 2004/0094873 A1 * | 5/2004 | Dubson | A61L 27/56 427/457 |
| 2006/0083776 A1 * | 4/2006 | Bott | A61L 15/58 424/445 |
| 2007/0131805 A1 * | 6/2007 | Yamaguchi | B05B 5/005 239/690 |
| 2009/0233057 A1 * | 9/2009 | Aksay | D01D 5/0038 427/469 |
| 2009/0311587 A1 * | 12/2009 | Best | H01M 50/105 429/127 |
| 2010/0018641 A1 | 1/2010 | Branham et al. | |
| 2010/0152880 A1 * | 6/2010 | Boyden | A61K 51/1244 700/283 |
| 2011/0256397 A1 * | 10/2011 | Tojo | A61L 15/42 156/308.6 |
| 2012/0214375 A1 * | 8/2012 | Kitano | B01D 39/2065 423/447.2 |
| 2012/0301567 A1 * | 11/2012 | Pokorny | D01D 5/0076 425/174.8 E |
| 2013/0122069 A1 * | 5/2013 | Tojo | A61K 8/027 424/443 |
| 2013/0125912 A1 * | 5/2013 | Tojo | D04H 1/43838 428/398 |
| 2013/0142852 A1 * | 6/2013 | Tojo | A61K 8/027 424/443 |
| 2013/0312638 A1 * | 11/2013 | Parker | D01D 5/0069 264/211.1 |
| 2014/0322515 A1 * | 10/2014 | Parker | D01D 5/0985 428/221 |
| 2016/0168755 A1 | 6/2016 | Toyoda et al. | |
| 2018/0073165 A1 | 3/2018 | Laidmäe et al. | |
| 2018/0317627 A1 * | 11/2018 | Fukuda | B05B 12/124 |
| 2019/0053602 A1 | 2/2019 | Amari et al. | |
| 2019/0119830 A1 * | 4/2019 | Janssen | D04H 1/70 |
| 2019/0153623 A1 | 5/2019 | Sugawara et al. | |
| 2019/0343731 A1 | 11/2019 | Amari et al. | |
| 2020/0039837 A1 * | 2/2020 | Umebayashi | D01D 5/0015 |
| 2020/0263323 A1 * | 8/2020 | Sivler | D01F 13/00 |
| 2020/0406542 A1 * | 12/2020 | Bennett | B29C 64/35 |

FOREIGN PATENT DOCUMENTS

| | | |
|---|---|---|
| CN | 207362375 U | 5/2018 |
| EP | 3 218 536 B1 | 5/2019 |
| JP | 2006-241629 A | 9/2006 |
| JP | 2007-92210 A | 4/2007 |
| JP | 2011-32613 A | 2/2011 |
| JP | 2011-84843 A | 4/2011 |
| JP | 2016-32780 A | 3/2016 |
| JP | 2020-179949 A | 11/2020 |
| JP | 2021-70906 | 5/2021 |
| KR | 10-2016-0020262 A | 2/2016 |
| KR | 10-2016-0020264 A | 2/2016 |
| KR | 10-2017-0130500 A | 11/2017 |
| WO | WO 2014/125407 A1 | 8/2014 |
| WO | WO 2015/020129 A1 | 2/2015 |
| WO | WO 2017/069079 A1 | 4/2017 |
| WO | WO 2018/124227 A1 | 7/2018 |

OTHER PUBLICATIONS

U.S. Appl. No. 17/772,472, filed Apr. 27, 2022, Tomonari Okada, et al.
Written Opinion dated Dec. 1, 2020, in PCT/JP2020/040151 (with English Translation).
International Search Report dated Dec. 1, 2020 in PCT/JP2020/040153 filed on Oct. 26, 2020, 3 pages.

\* cited by examiner

FIBER DEPOSIT PRODUCTION METHOD, MEMBRANE PRODUCTION METHOD, AND MEMBRANE ADHESION METHOD

CROSS-REFERENCE TO RELATED APPLICATIONS

The present application is a 35 U.S.C. § 371 national stage application of International patent application PCT/JP2020/040153, filed Oct. 26, 2020, which is based on and claims the benefit of priority to Japanese Application No. 2019-195659 and Japanese Application No. 2019-195709, both filed Oct. 28, 2019. The entire contents of these applications are incorporated herein by reference.

TECHNICAL FIELD

The present invention relates to a method for producing a fiber deposit, a method for producing a film, and a method for attaching a film.

BACKGROUND ART

Various techniques have been proposed for producing fibers and deposits thereof by electro spinning. For example, Patent Literature 1 discloses a method of using a woven fabric including an electroconductive material, and producing a fiber structure on the woven fabric by electro spinning. Patent Literature 2 discloses a method for producing a nanofiber film made from a polymer substance by using a collection sheet in which deposit regions, where fibers are to be deposited, and non-deposit regions, where fibers are not deposited, coexist on a target surface on which the nanofiber film is to be formed.

Patent Literature 3 discloses an electro-spraying device with which a solution material sprayed from a nozzle is deposited on a substrate as a thin film. The Patent Literature discloses that this device includes: the aforementioned nozzle for spraying the solution material in a voltage-applied state; and a mask arranged between the nozzle and the substrate in the vicinity of the substrate, the mask including a first mask portion and a second mask portion arranged separate from one another in a planar view, and long narrow connection portions for connecting the first mask portion and the second mask portion and located separate from the substrate.

Applicant has previously proposed a coating formation method involving an electrostatic spraying step for electrostatically spraying, directly onto a coating formation target, a composition that contains a polymer having coating formability, to thereby form a coating constituted by a deposit including fibers (Patent Literature 4).

CITATION LIST

Patent Literature

Patent Literature 1: JP 2007-92210A
Patent Literature 2: JP 2011-84843A
Patent Literature 3: JP 2016-32780A
Patent Literature 4: WO 2018/124227

SUMMARY OF INVENTION

The present invention relates to a method for producing a fiber deposit, including: collecting a fiber with a fiber collection tool, the fiber being spun by a user by performing electrospinning using an electrospinning device; and producing a deposit of the fiber on a surface of the fiber collection tool.

In one embodiment, a fiber collection tool including, in its interior, an electroconductive section is used as the fiber collection tool.

The present invention also relates to a method for producing a film on a surface of an object, the film including a fiber deposit.

In one embodiment, the method involves collecting, with a fiber collection tool, a fiber spun by a user by performing electrospinning using an electrospinning device, and forming a film including a deposit of the fiber on a surface of the fiber collection tool.

In one embodiment, the method involves pressing the fiber collection tool, having the film formed thereon, against a surface of an object and transferring the film onto the surface of the object, to form the film including the fiber deposit on the surface of the object.

The present invention also relates to a method for attaching a film.

In an embodiment, the method involves collecting, with a fiber collection tool, a fiber spun by a user by performing electrospinning using an electrospinning device, and forming a film including a deposit of the fiber on a surface of the fiber collection tool.

In an embodiment, the method involves pressing the fiber collection tool, having the film formed thereon, against a surface of an object, and attaching the film onto the surface of the object.

DESCRIPTION OF EMBODIMENTS

Figure 1:
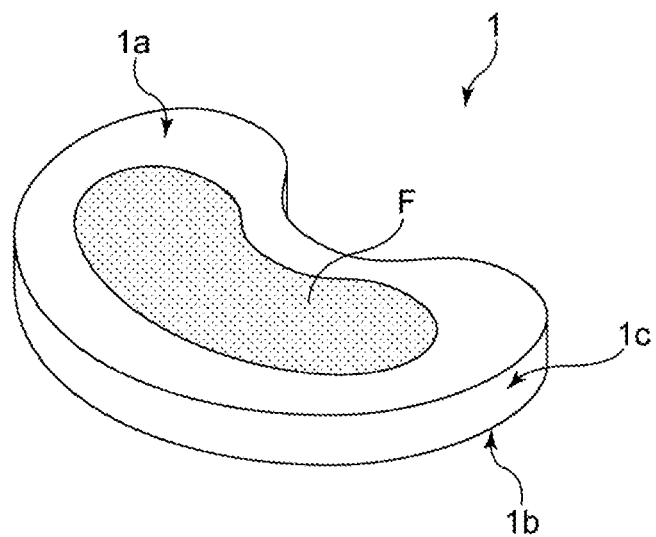
FIG. 1 is a perspective view schematically illustrating an embodiment of a fiber collection tool used in a production method according to the present invention.

Production of fiber deposits formed by electrospinning may be performed in non-industrial environments, such as at home, depending on the use thereof. Hence, there is a demand for a method with which electrospinning can be performed easily while maintaining fiber spinnability. Unfortunately, the techniques disclosed in Patent Literatures 1 to 3 use stationary electrospinning devices, and thus cannot perform electrospinning conveniently.

Further, such fiber deposits may be used for aesthetic purposes, such as for makeup or skin care. Particularly, from the viewpoint of achieving a desired finish in makeup and applying skin care in desired areas, it is also desirable that the user can produce a fiber deposit having a desired shape/size through the user's own operation. Unfortunately, the techniques disclosed in Patent Literatures 1 to 3 give no consideration to producing a fiber deposit through the user's own operation.

The method disclosed in Patent Literature 4 involves a method for performing electrospinning easily while maintaining fiber spinnability. However, no consideration is given to film-formation targets that can suitably be used for electrospinning, and there is still room for improvement in this regard.

Further, although Patent Literature 4 discloses a method in which electrospinning is directly performed on a surface of a target through the user's own operation, this method is hard to apply to areas, such as the eyes, where it is difficult to perform electrospinning directly, and there is still room for improvement also in this regard.

The present invention relates to a fiber deposit production method, a film production method, and a film attachment method capable of overcoming the drawbacks of conventional art.

The present invention will be described below according to preferred embodiments thereof with reference to the drawings. A fiber collection tool suitably usable in a production method or an attachment method according to the present invention is used to collect, preferably directly, a fiber spun by electrospinning. Electrospinning is a method for spinning a fiber, wherein: a positive or negative high voltage is applied to a material liquid containing a resin, which is a material of the fiber, to thereby charge the material liquid; and the charged material liquid is ejected toward an object. The ejected material liquid spreads out into space while repeatedly being stretched and becoming finer by Coulomb repulsion force, and fine fiber with a small fiber diameter is deposited on a surface of the object. In this way, a fiber deposit—preferably, a film including a fiber deposit—can be obtained. The material liquid will be described in detail further below.

The fiber collection tool has a size holdable in a hand of a user forming the fiber or the fiber deposit. Herein, "holdable by the hand" encompasses embodiments wherein the fiber collection tool is gripped and held with the hand, and also embodiments wherein the fiber collection tool is pinched and held with the fingers and embodiments wherein the fiber collection tool is placed on the palm, the back of the hand, etc., and held thereon.

The size of the fiber collection tool is not particularly limited so long as it is holdable by the hand, but it is preferable that the mass of the fiber collection tool is preferably 500 g or less, more preferably 200 g or less. The maximum length spanning the fiber collection tool is preferably from 0.1 mm to 30 cm. The volume of the fiber collection tool is preferably from 0.5 $cm^3$ to $10^4$ $cm^3$. The above is preferable because, in this way, the fiber collection tool can be held not only with one hand, but can also be placed on other areas such as the knee, and further, the fiber collection tool can easily be taken along and carried and also operated easily, thereby allowing fibers formed on the fiber collection tool to be easily applied or transferred to an application area with the hand.

The three-dimensional shape of the fiber collection tool is not particularly limited so long as the fiber spun by electrospinning can be collected, and may be, for example, a three-dimensional shape including a plurality of planar portions, a three-dimensional shape including a plurality of curved portions having different curvatures, or a three-dimensional shape including the aforementioned planar portions and curved portions. Concrete examples of three-dimensional shapes may include: prismatic shapes such as a triangular prism, a quadrangular prism, a pentagonal prism, etc.; circular cylindrical shapes such as a circular cylinder, an elliptic cylinder, etc.; pyramidal shapes such as a triangular pyramid, a quadrangular pyramid, a pentagonal pyramid, etc.; circular conic shapes such as a circular cone, an elliptic cone, etc.; convex polyhedrons such as an octahedron, a dodecahedron, etc.; non-convex polyhedrons such as a star-shaped polyhedron, etc.; and other three-dimensional shapes such as a plate shape, a sheet-like shape, a spherical shape, an ellipsoidal shape, a fan shape, a mesh shape, etc. In cases where the fiber collection tool has a three-dimensional shape having apexes, it is preferable that at least one apex is rounded.

The planar-view shape of the fiber collection surface of the fiber collection tool is also not particularly limited so long as the fiber spun by electrospinning can be collected, and may be, for example, a shape including a plurality of rectilinear portions in its contour, a shape including a plurality of curvilinear portions with different curvatures in its contour, or a shape including both the aforementioned rectilinear portions and curvilinear portions in its contour, Concrete examples may include: polygonal shapes such as a triangle, a quadrangle, a rhombus, a pentagon, etc.; circular shapes such as a semicircle, a perfect circle, an ellipse, etc.; and planar shapes including both curvilinear portions and rectilinear portions in its contour, such as a star shape, a crescentic shape, a lattice shape, etc. In cases where the fiber collection tool has a planar shape having apexes, at least one apex may be rounded. The fiber collection surface of the fiber collection tool 1 may be a flat surface or a curved surface at the time of spinning fibers. In cases where the fiber collection surface of the fiber collection tool 1 is a curved surface, it may be a convex shape projecting outward from the fiber collection tool 1, or may be a concave shape depressed inward into the fiber collection tool 1.

FIG. 1 schematically illustrates an embodiment of a fiber collection tool. The fiber collection tool 1 illustrated in the figure has a plate shape having surfaces constituted by: a pair of substantially flat principal surfaces 1a, 1b; and a side surface 1c intersecting with the principal surfaces. Preferably, one of the principal surfaces 1a, 1b is used as the fiber collection surface. The fiber collection tool 1 illustrated in the figure has a pair of crescentic principal surfaces 1a, 1b with rounded apexes. It is preferable that the fiber collection tool 1 has no corners, such as by rounding the apexes and ridgelines. The presence of a corner is likely to cause electric charge to concentrate thereon, whereas a shape with no corner suppresses electric charge from concentrating on a portion of the fiber collection tool 1, which facilitates fibers to be deposited uniformly on the fiber collection tool 1. A "corner" is a section formed by two plane surfaces, or a plane surface and a curved surface, intersecting with one another. In the fiber collection tool 1 of the present embodiment, the first principal surface 1a is used as the fiber collection surface, and a deposit F of fiber, preferably a film F constituted by a deposit of fiber (referred to hereinafter simply as "fiber deposit" or "film"), is formed directly in a partial region of the first principal surface 1a. For the sake of explanation, hereinbelow, "fiber deposit" and "film" are treated as synonymous unless particularly stated otherwise.

It is preferable that the fiber collection tool 1 has one or a plurality of depressions in the surface thereof. The use of a fiber collection tool having depression(s) can reduce the contact area between the fiber collection tool 1 and the film F, and thereby, the film F formed on the surface of the fiber collection tool 1 can be peeled off from the fiber collection tool 1 easily, and transferability can be further improved. The depression may be a through hole, or a penetrating groove such as a slit. Alternatively, the depressions may be micropores in a porous body such as a sponge. For the material of the fiber collection tool including depressions, it is possible to use a porous body, for example. For the porous body, it is possible to use the examples described further below.

Herein, "transferability (transferring properties)" means pressing a film including a fiber deposit against an object and attaching the film onto the object.

It is preferable that the fiber collection tool 1 has, on the surface thereof, a section including napped fiber. A "napped section" may be a section in which short fibers are fixed on the surface in a standing state. The use of a fiber collection tool having a napped section can reduce the contact area between the fiber collection tool 1 and the film F, and thereby, transferability can be further improved. An example of a fiber collection tool having a napped section includes a cosmetic puff subjected to electrostatic flocking.

It is preferable that an agent having an action of releasing the film F is applied to a surface of the fiber collection tool. Stated differently, the fiber collection tool has, on the surface thereof, an agent having an action of releasing the film F. Using such a fiber collection tool can further improve transferability. In this case, in the aforementioned method for forming the film F, an agent having an action of releasing the film F is applied in advance to the surface of the fiber collection tool. For example, the agent may be applied to a portion or the entire region of the collection surface of the fiber collection tool, and then the later-described method for producing the fiber deposit (film) may be performed.

From the viewpoint of further facilitating peeling of the film F from the fiber collection tool 1, it is preferable that the agent having a releasing action is a powdery agent. Examples of the powdery agent may include: inorganic powders, such as silicic acid, silicic acid anhydride, magnesium silicate, talc, sericite, mica, kaoline, colcothar, clay, bentonite, mica, titanium-coated mica, bismuth oxychloride, zirconium oxide, magnesium oxide, titanium oxide, zinc oxide, aluminum oxide, calcium sulfate, barium sulfate, magnesium sulfate, calcium carbonate, magnesium carbonate, iron oxide, ultramarine blue, chromium oxide, chromium hydroxide, calamine, carbon black, boron nitride, and composites thereof; organic powders, such as polyamide, nylon, polyester, polypropylene, polystyrene, polyurethane, vinyl resins, urea resins, phenolic resins, fluorocarbon resins, silicon resins, acrylic resins, melamine resins, epoxy resins, polycarbonate resins, divinylbenzene styrene copolymer, silk powder, cellulose, metal salts of long-chain alkyl phosphates, N-mono-long-chain alkyl acyl basic amino acids, and composites thereof; and composite powders including the aforementioned inorganic powder(s) and organic powder(s). The aforementioned powdery agents may be colored or non-colored (e.g., may be white or substantially transparent).

From the viewpoint of easily forming an electrical conduction path between the fiber collection tool 1 and an electrospinning device 10 and improving the spinnability by electrospinning, it is preferable that the fiber collection tool 1 has one of the following configurations (1) to (3) for improving electroconductivity. Each of these configurations will be described below.

(1) The fiber collection tool 1 includes an electroconductive section in at least a portion of the surface thereof.
(2) The fiber collection tool 1 includes a hydrophilic section in at least a portion of the surface thereof.
(3) The fiber collection tool 1 includes an electroconductive section in the interior thereof.

First, a fiber collection tool having the aforementioned configuration (1) will be described in detail. The fiber collection tool having the configuration (1) includes an electroconductive section in at least a portion of the surface thereof. The electroconductive section is a section for forming, during fiber spinning by electrospinning, an electrical conduction path between the fiber collection tool 1 held by the human hand and an electrospinning device, to thereby enable fiber spinning by electrospinning. In addition, the electroconductive section is a section on which the fiber spun by electrospinning is deposited.

The electroconductive section present on the surface of the fiber collection tool 1 may be formed continuously and uniformly over the surface of the fiber collection tool 1, or may be formed in only a portion of the surface of the fiber collection tool 1. In cases where the electroconductive section is formed in only a portion of the surface, it is preferable that the electroconductive section is formed continuously, and more preferably, formed so as to extend to a region, or vicinity thereof, that can be touched by a portion of the user's body. Note that this does not prevent the electroconductive section from also being formed inside the fiber collection tool 1.

From the viewpoint of improving fiber spinnability of by electrospinning and performing spinning of fiber easily, it is preferable that the fiber collection tool 1 has electroconductive sections respectively on the fiber collection surface and at the section to contact the user's body, and it is further preferable that the electroconductive section on the fiber collection surface is formed continuously with the electroconductive section at the section to contact the user's body, and it is even more preferable that the electroconductive section is formed continuously over the entire region of the surface of the fiber collection tool 1. Forming the electroconductive section continuously over the entire region of the surface of the fiber collection tool 1 is advantageous, in that spinning and depositing of fiber can be performed even more easily, because there is no need to particularly take into consideration the orientation of the fiber collection tool 1 during electrospinning or the position in which the fiber collection tool 1 is held.

The electroconductive section present on the surface of the fiber collection tool 1 preferably has a surface electrical resistivity value of preferably $10^{11}$ $\Omega/cm^2$ or less, more preferably $8.0 \times 10^{10}$ $\Omega/cm^2$ or less, even more preferably $5.0 \times 10^{10}$ $\Omega/cm^2$ or less, even more preferably $10^{10}$ $\Omega/cm^2$ or less; the lower the value is, the more preferable. However, the surface electrical resistivity value is realistically $10^0$ $\Omega/cm^2$ or greater. By having such surface electrical resistivity, spinning of fiber by electrospinning can be performed efficiently, and the fiber deposit can be formed in a desired position of the fiber collection tool 1. Such an electroconductive section can be formed, for example, by using the later-described material, or by subjecting the surface of the material to a treatment to increase electroconductivity. The surface electrical resistivity of the electroconductive section may be the same among various electroconductive sections, or may be different among various electroconductive sections within the aforementioned range of surface electrical resistivity.

From the viewpoint of easily enabling spinning of fiber by electrospinning, it is further preferable that the surface electrical resistivity value of the fiber collection tool 1 is within the aforementioned range at any discretionary position on the surface thereof. Stated differently, it is further preferable that the electroconductive section having a surface electrical resistivity within the aforementioned range is formed continuously over the entire region of the surface of the fiber collection tool 1.

The surface electrical resistivity can be measured, for example, according to the method of JIS K6911 (1995). More specifically, a measurement sample is obtained by cutting a fiber collection tool 1 being measured such that the surface in which the surface electrical resistivity is to be measured is 50 mm long and 45 mm wide, and the thickness is 4 mm. The measurement sample's surface to be measured is brought into contact with an inner electrode and a ring electrode of a Chamber R12704 from Advantest Corporation, so as to bridge the inner electrode and the ring electrode. In this state, using an electrical resistance meter R8340A from Advantest Corporation in Surface mode, a voltage is applied to the electrodes such that the potential difference between the chamber's electrodes becomes 500 V, and the resistivity ($\Omega/cm^2$) is measured. Measurement is performed in a temperature-humidity environment at room temperature of 22 to 23° C. and a relative humidity of 46%.

Examples of materials for the fiber collection tool 1 having the aforementioned configuration (1) may include fiber sheets, films, porous bodies, elastic bodies, etc. One of these materials may be used singly, or a plurality of these materials may be used in combination.

Examples of fiber sheets may include various nonwoven fabrics, woven fabrics, knitted fabrics, paper, mesh sheets, and laminates thereof.

Examples of films may include mesh films made from resin materials, such as polyethylene and polypropylene, and various film sheets.

Examples of porous bodies may include foams, with concrete examples including foams including, as a material, polyurethane, wet urethane, acrylonitrile•butadiene copolymer (NBR), styrene•butadiene copolymer (SBR), natural rubber (NR), ethylenepropylenediene copolymer (EPDM), melamine foam, polyvinyl alcohol (PVA), cellulose, etc.

Examples of elastic bodies may include rubber products and elastomer products, with concrete examples including rubber-made meshes, various rubber sheets, and foamed rubber (rubber sponges) including, as a material, one or more rubber-like substances such as natural rubber, synthetic rubber, silicone rubber, acrylic rubber, urethane rubber, nitrile rubber, etc.

The aforementioned materials may be used as is, or the materials may include an electroconductive material made, for example, by subjecting at least a surface of the aforementioned material to a treatment for increasing electroconductivity, such as a hydrophilizing treatment or an electroconductive treatment. Examples of treatments for increasing electroconductivity may include: mixing, coating or immersion of the aforementioned material with/in a liquid electroconductive material such as water, a surfactant, etc.; and mixing or coating of an electroconductive material such as copper, carbon, etc.

Among the various types of materials described above, it is preferable that the fiber collection tool 1 includes a porous material, and is more preferably a monolithic molded body of a porous material. This structure is advantageous in that the film F including a fiber deposit can be deposited on the surface of the fiber collection tool 1 in a manner easily peelable from the fiber collection tool 1. Examples of usable porous materials may include the aforementioned fiber sheets and porous bodies, as well as materials obtained by subjecting these to a treatment for improving electroconductivity, so that the material includes an electroconductive material in the surface and/or interior thereof. The fiber collection tool 1 may include a plurality of molded bodies of porous materials in combination, so long as electrospinning can be performed. In this case, it is preferable that the electroconductive sections of the respective molded bodies are electrically connected.

It is preferable that the fiber collection tool 1 includes an elastic material, and is more preferably a monolithic molded body of an elastic material. With this structure, the shape of the fiber collection tool 1 can be deformed easily by application of gripping force, while maintaining excellent fiber spinnability. So, by changing the shape of the fiber collection surface, spinning can be performed so that the range for forming the fiber deposit and the planar shape thereof can take on a desired range and shape.

Examples of elastic materials may include the aforementioned fiber sheets, porous bodies, and elastic bodies, as well as materials obtained by subjecting these to a treatment for improving electroconductivity, so that the material includes an electroconductive material in the surface and/or interior thereof. The fiber collection tool 1 may include a plurality of molded bodies of elastic materials in combination, so long as the effects of the present invention are achieved. In this case, it is preferable that the electroconductive sections 2 of the respective molded bodies are electrically connected.

Particularly, it is preferable that the fiber collection tool 1 having the aforementioned configuration (1) includes a porous and elastic material, and is more preferably a monolithic molded body of such a material. With this structure, the contact area between the fiber collection tool 1 and the film F is reduced by the pores formed in the surface of the porous material, and thus, the film F formed on the surface of the fiber collection tool 1 can be peeled off easily from the fiber collection tool 1, thus improving the productivity of the film F. In addition, by using an elastic material, the shape of the fiber collection tool 1 can be deformed easily by application of gripping force, while maintaining excellent fiber spinnability. So, by changing the shape of the fiber collection surface, spinning can be performed so that the range for forming the film F and the planar shape thereof can take on a desired range and shape. Examples of such a porous and elastic material may include porous bodies such as foams, e.g., polyurethane, wet urethane, acrylonitrile•butadiene copolymer (NBR), melamine foam, etc., as well as materials obtained by subjecting these to a treatment for improving electroconductivity, so that the material includes an electroconductive material in the surface and/or interior thereof. The fiber collection tool 1 may include, in combination, a plurality of molded bodies of elastic materials constituted by porous materials, so long as electrospinning can be performed. In this case, it is preferable that the electroconductive sections of the respective molded bodies are electrically connected.

In cases where at least one of the electroconductive section 2 or surface section 3 constituting the fiber collection tool 1 includes a porous body, pores formed in the porous body may be connected (open) pores, independent (closed) pores, or a combination thereof. In either case, the pore diameter of the porous body is preferably 10 μm or greater, more preferably 20 μm or greater, and preferably 1000 μm or less, more preferably 900 μm or less. For example, the pore diameter can be measured by: observing the material with, for example, a scanning electron microscope (SEM) under a magnification of 500×; discretionarily choosing 10 porous holes (pores) from the two-dimensional image; directly reading off the maximum lengths thereof; and finding the arithmetic mean value thereof as the porous body's pore diameter.

The apparent density of the porous body is preferably 0.001 g/cm$^3$ or greater, more preferably 0.005 g/cm$^3$ or greater, and preferably 10 g/cm³ or less, more preferably 5 g/cm³ or less. For example, the apparent density can be measured by: finding the mass (g) of the sample with a device capable of measuring mass up to 0.001 g; also measuring, with vernier calipers, dimensions necessary for calculating the volume, such as the sample's diameter or area and the sample's thickness under no-load, and calculating the sample's volume (cm³); and calculating the apparent density of the porous body by the formula "mass (g)/volume (cm³)".

In cases where the fiber collection tool 1 includes an elastic material, the hardness of the material is preferably 1 or greater, more preferably 5 or greater, and preferably 95 or less, more preferably 90 or less, as measured with a rubber hardness meter. For example, the material hardness can be measured by: bringing a pressurizing surface of an indentor of a rubber hardness meter (ASKER Type FP) perpendicularly into contact with a side surface of a test piece at 20° C., 50% RH; applying pressure for 3 seconds in this state; and reading the meter scale at that time.

A fiber collection tool having the aforementioned configuration (2) will be described in detail. The fiber collection tool having the configuration (2) includes a hydrophilic section in at least a portion of the surface thereof. The hydrophilic section is a section having hydrophilicity, i.e., a section having affinity for water and having water absorbable/retainable properties. The hydrophilic section has, for example, a water contact angle of 90° or less at 25° C. Including such a hydrophilic section will increase the electroconductivity of the fiber collection tool 1, thus making it possible to improve fiber spinnability by electrospinning through an electrical conduction path formed between the fiber collection tool 1 and a later-described electrospinning device. Herein, "spinnability" refers to formation of fiber from a fiber material liquid and depositing of the fiber onto a target position. From the viewpoint of depositing the spun fiber onto the fiber collection tool 1 more effectively, it is preferable that the hydrophilic section has a water contact angle at 25° C. of preferably 15° or greater, more preferably 18° or greater, and preferably from 15° to 90°, more preferably from 18° to 90°.

The contact angle between the hydrophilic section and water may be the same among various hydrophilic sections, or may be different among various hydrophilic sections within the aforementioned range of water contact angle. The contact angle with water at 25° C. is measured according to the following method.

Method for Measuring Contact Angle at 25° C.:

The measurement environment is set to air temperature of 25° C. and relative humidity of 50±5% RH. A 0.5-μL droplet of ion-exchanged water is dropped onto a surface of the fiber collection tool for which the contact angle is to be measured, and the liquid droplet is video-recorded from a side where the interface between the liquid droplet and the surface being measured can be viewed. The contact angle is measured based on the recorded image. For the measurement device, for example, an automatic contact angle meter, DM501Hi from Kyowa Interface Science Co., Ltd., is used. An image in which the contour of the liquid droplet is clear is selected from among images obtained after 20 seconds from liquid dropping, and in the selected image, the contact angle of the liquid droplet is measured based on a reference surface, to find the water contact angle at 25° C.

In cases where the fiber collection tool has micropores in its surface, as in a porous body etc., it may not be possible to measure the contact angle of the fiber collection tool stably. In such cases, an article made from the same material as the material forming the fiber collection tool but having no micropores in its surface is used for the measurement, instead of the fiber collection tool.

From the viewpoint of improving electroconductivity, it is preferable that the hydrophilic section has water absorbency. More specifically, the water absorption time of the hydrophilic section when 0.1 mL of water is dropped at 25° C. is preferably from 0 seconds to 4 hours, more preferably from 0 seconds to 3.5 hours, even more preferably from 0 seconds to 2.25 hours.

Method for Measuring Water Absorption Time at 25° C.:

The method is performed with reference to Water Absorption Rate (Dropping Method) in "Testing Methods for Water Absorbency of Textiles" in the Japanese Industrial Standard (JIS L 1907:2004). The measurement environment is set to air temperature of 25° C. and relative humidity of 50±5% RH. A summary of the measurement method is as follows. A 0.1-mL droplet of ion-exchanged water is dropped onto a measurement surface of the fiber collection tool where water is to be absorbed, and an image of the liquid droplet on the measurement surface is captured from above, to measure the water absorption time based on the captured image. The light source used for the observation is a fluorescent lamp (brightness: 500 to 1000 1x) with which the specular reflection of water can be observed with the eyes.

First, a paper napkin is placed on a flat plastic tray, and the fiber collection tool is placed thereon with the measurement surface facing upward. The fiber collection tool is made into a test piece having a size of 40×50×20 mm, and 0.1 mL of water is dropped with a micropipette (Eppendorf Multipette M4 (registered trademark)) from a distance of around 1 cm from the fiber collection tool. A timer is used to measure, by seconds, the length of time from when the water droplet reaches the surface of the test piece to when the specular reflection disappears and only moisture remains due to the water droplet being absorbed by the test piece. Note that, in cases where water is not absorbed even after 6 hours, it is determined that measurement is not possible because the water droplet evaporates spontaneously, and "Over 6 hours" is recorded as the measurement result.

The hydrophilic section having the aforementioned properties can be formed, for example, by using the later-described materials, or by subjecting the surface of the material to a treatment to increase hydrophilicity.

The hydrophilic section of the fiber collection tool 1 may be formed over the entire region of the surface of the fiber collection tool 1, or may be formed in a portion of the surface of the fiber collection tool 1. From the viewpoint of further improving fiber spinnability, in cases where the hydrophilic section is formed in a portion of the surface of the fiber collection tool 1, it is preferable that the hydrophilic section is formed on the surface of the fiber collection tool 1 where the spun fibers are collected and deposited. For example, in the fiber collection tool 1 of the present embodiment, it is preferable that the hydrophilic section is formed on one of the pair of principal surfaces 1a, 1b, and more preferable that the hydrophilic section is formed on both the principal surfaces 1a, 1b.

From the viewpoint of easily collecting fiber by electrospinning, it is further preferable that the water contact angle of the fiber collection tool 1 is within the aforementioned range at any discretionary position on the surface thereof. Stated differently, it is further preferable that the hydrophilic section having a water contact angle within the aforementioned range is formed continuously over the entire region of the surface of the fiber collection tool 1.

From the viewpoint of forming the hydrophilic section more easily, it is preferable that a material for forming the fiber collection tool 1 is subjected to a hydrophilizing treatment. For the hydrophilizing treatment, it is possible to employ any known method, such as mixing, coating or immersion of the material forming the fiber collection tool 1 with/in a hydrophilic base material or a surfactant. The hydrophilizing treatment may be a pre-treatment performed before forming the fiber collection tool 1, or may be a post-treatment performed after forming the fiber collection tool 1. An example of a method for performing the hydrophilizing treatment as a pre-treatment may include a method disclosed in JP 2015-131875A, wherein a surfactant, such as an aliphatic diester compound, is added to a material for forming the fiber collection tool 1, and then the fiber collection tool 1 is molded. Examples of methods for performing the hydrophilizing treatment as a post-treatment may include methods disclosed in JP S63-268751A and JP H1-81834A, wherein the formed fiber collection tool 1 is immersed in an aqueous solution containing a hydrophilic base material, such as polyethylene glycol·dimethacrylate, and then heating the same, to graft-polymerize the hydrophilic base material onto the material forming the fiber collection tool 1.

Examples of surfactants in the hydrophilic section may include cationic surfactants, anionic surfactants, amphoteric surfactants, nonionic surfactants, etc.

Examples of cationic surfactants may include: alkyl trimethyl ammonium bromides selected from, for example, cetyl trimethyl ammonium bromide, behenyl trimethyl ammonium chloride, distearyl dimethyl ammonium chloride, tricetyl methyl ammonium chloride, and stearyl dimethyl benzyl ammonium chloride; alkyl dimethyl ammonium chlorides selected from, for example, dicetyl dimethyl ammonium chloride, distearyl dimethyl ammonium chloride, diaralkyl dimethyl ammonium chloride, and dibehenyl dimethyl ammonium chloride; quaternary ammonium salts such as benzalkonium chloride; and dimethyl distearyl ammonium salts.

Examples of anionic surfactants may include: fatty acid salts derived from fatty acids having 8 or more carbon atoms, such as sodium laurate, potassium palmitate, etc.; alkyl sulfate salts such as sodium lauryl sulfate, potassium lauryl sulfate, sodium stearyl sulfate, etc.; alkyl ether sulfate salts such as triethanolamine polyoxyethylene lauryl sulfate, etc.; N-acyl sarcosine salts such as lauroyl sarcosine sodium salt, etc.; N-acyl methyl taurine salts such as N-myristoyl-N-methyltaurine sodium salt, etc.; N-acyl fatty acid glutamate salts such as sodium N-myristoyl-L-glutamate, disodium N-stearoyl glutamate, monosodium N-lauroyl myristoyl-L-glutamate, triethanolamine N-cocoyl glutamate, etc.; sulfosuccinate salts such as sodium di-2-ethylhexyl sulfosuccinate, etc.; and polyoxyethylene alkyl ether phosphate salts such as sodium polyoxyethylene cetyl ether phosphate, etc.

Examples of amphoteric surfactants may include stearyl betaine, lauryl betaine, etc.

Examples of nonionic surfactants may include: ethylene glycol fatty acid esters such as ethylene glycol monostearate, etc.; polyethylene glycol fatty acid esters such as polyethylene glycol (2) monostearate, etc.; polyalkylene glycol alkyl ethers such as polyethylene glycol (5) decyl pentadecyl ether, etc.; polyethylene glycol hydrogenated castor oil such as polyethylene glycol (5) hydrogenated castor oil monoisolaurate, etc.; propylene glycol fatty acid esters; monoglycerin mono-fatty acid esters such as glycerin monoisostearate, etc.; monoglycerin di-fatty acid esters such as glycerin distearate, glycerin dilaurate, etc.; glycerin alkyl ethers such as glycerin monoisostearyl ether, etc.; sorbitan fatty acid esters such as sorbitan monostearate, etc.; fatty acid alkanolamides; fatty acid dialkanol amides such as lauric acid diethanolamide, etc.; and polyoxyethylene sorbitan fatty acid esters such as polyoxyethylene sorbitan monostearate, etc.

One type of surfactant selected from the above may be used, or two or more types may be used in combination.

From the viewpoint of providing the hydrophilic section with a water contact angle within the aforementioned range more reliably, it is preferable that a surfactant is present in the fiber collection tool 1. From the same viewpoint as described above, the content of the surfactant in the fiber collection tool 1 is preferably 0.01 mass % or greater, more preferably 0.05 mass % or greater, and preferably 35 mass % or less, more preferably 30 mass % or less, and preferably from 0.01 to 35 mass %, more preferably from 0.05 to 30 mass %.

From the viewpoint of easily deforming the shape of the fiber collection tool 1, it is preferable that the fiber collection tool 1, having the aforementioned configuration (2), has elasticity along a direction in which the spun fiber is collected and deposited. For example, the fiber collection tool 1 of the present embodiment has elasticity along the thickness direction. In cases where the fiber collection tool 1 has elasticity, it is preferable that the hardness, as measured with the aforementioned rubber hardness meter (ASKER Type FP) at 20° C., 50% RH, is within the same range as the fiber collection tool having the aforementioned configuration (1).

For materials of the fiber collection tool 1 having the aforementioned configuration (2), it is possible to use the same materials as those described above as examples of materials for the fiber collection tool having the aforementioned configuration (1). Particularly, it is preferable that the material is, for example, a laminate formed by layering fiber sheets, a porous body, or an elastic material such as rubber. One of these materials may be used singly, or a plurality of these materials may be used in combination. These materials may be used as is, or a material obtained by subjecting at least a surface of the aforementioned material to the aforementioned hydrophilizing treatment may be used.

It is preferable that the fiber collection tool 1 having the aforementioned configuration (2) includes a porous material, and is more preferably a monolithic molded body of such a material. With this structure, the contact area between the pores formed in the surface of the porous material and the deposited fiber is reduced, and thus, the film F formed on the surface of the fiber collection tool 1 can be peeled off easily from the fiber collection tool 1, thus improving the productivity of the film F. The porous material may be as described in the explanation on the fiber collection tool having the aforementioned configuration (1).

Figure 2:
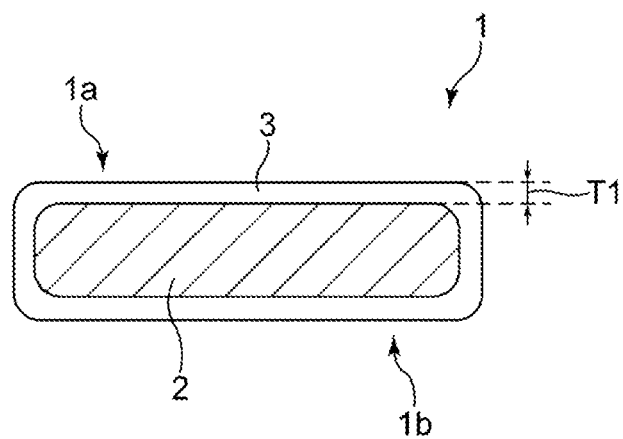
FIG. 2 is a cross-sectional view schematically illustrating another embodiment of a fiber collection tool used in a production method according to the present invention.

A fiber collection tool having the aforementioned configuration (3) will be described in detail. An embodiment of a fiber collection tool having the configuration (3) is schematically illustrated in FIG. 2. As illustrated in the figure, the fiber collection tool 1 preferably includes, in its interior, an electroconductive section 2. The electroconductive section 2 is a section for forming, during fiber spinning by electrospinning, an electrical conduction path between the fiber collection tool 1 held by the human hand and a later-described electrospinning device, to thereby enable fiber spinning by electrospinning, even in cases where a later-described surface section 3 is non-electroconductive.

The electroconductive section 2 is a section that occupies a large portion of the fiber collection tool 1, and more specifically, occupies preferably 60 vol % or greater, more preferably 80 vol % or greater, or even 100 vol %, with respect to the volume of the fiber collection tool 1. In cases where the later-described surface section 3 is provided, the percentage of the electroconductive section 2 with respect to the volume of the fiber collection tool 1 is preferably 95 vol % or less.

The electroconductive section 2 present in the interior of the fiber collection tool 1 may be formed continuously over the entire region in the interior of the fiber collection tool 1 as illustrated in FIG. 2, or alternatively, may be formed in only a partial region of the interior of the fiber collection tool 1. In cases where the electroconductive section 2 is formed only in a portion of the interior, the electroconductive section 2 may be formed continuously, or a plurality of electroconductive sections 2 may be formed in a scattered manner, or a combination thereof may be employed.

It is preferable that the electroconductive section 2 is positioned so as to include the barycenter of the fiber collection tool 1, because in this way, the spun fiber can be deposited in a predetermined position. Note, however, that another electroconductive section may be present outside the electroconductive section 2 so long as the effects of the present invention can be achieved.

The fiber collection tool 1 has a volume electrical resistivity of preferably $10^{10}$ Ω·cm or less, more preferably $5 \times 10^9$ Ω·cm or less, even more preferably $10^9$ Ω·cm or less; the lower the value is, the more preferable. However, the volume electrical resistivity is realistically $10^0$ Ω·cm or greater. By having such volume electrical resistivity, spinning of fiber by electrospinning can be performed efficiently, and the fiber deposit can be formed in a concentrated manner in a desired position of the fiber collection tool 1, thus offering excellent targeting properties. For such a fiber collection tool 1, for example, a later-described material may be used for the electroconductive section 2, or a matter including an electroconductive material obtained by subjecting this material to a treatment for improving electroconductivity may be used for the electroconductive section 2. The electroconductive section 2 may be formed from two or more different sections, on condition that the volume electrical resistivity satisfies the aforementioned value.

The volume electrical resistivity can be measured, for example, according to the following method. First, the fiber collection tool 1 to be measured is sandwiched between an inner electrode and a counter electrode opposing the inner electrode in a chamber R12704 from Advantest Corporation with a pressure of 1 N/cm² applied thereto. Then, using an electrical resistance meter R8340A from Advantest Corporation in Volume mode, a voltage is applied to the electrodes such that the potential difference between the chamber's electrodes becomes 500 V, and the volume electrical resistivity (Ω·cm) is measured. Measurement is performed in a temperature-humidity environment at room temperature of 22 to 23° C. and a relative humidity of 46%.

From the viewpoint of retaining the electroconductive section 2 as well as improving fiber spinnability by electrospinning and also improving peelability of the spun fiber from the fiber collection tool 1, it is preferable that, as illustrated in FIG. 2, the fiber collection tool 1 has a surface section 3 formed outside the electroconductive section 2. The surface section 3 in the present configuration (3) preferably has a volume electrical resistivity different from the volume electrical resistivity of the electroconductive section 2. It is also preferable that the volume electrical resistivity of the surface section 3 is greater than the volume electrical resistivity of the electroconductive section 2. For example, in cases where the surface section 3 is thrilled in multi-layer form by a plurality of materials, the volume electrical resistivity may be measured from the interior of the fiber collection tool 1 toward the outside to find a boundary where the measurement value changes for the first time, and the inside of the boundary may be considered the electroconductive section 2 whereas the outside thereof may be considered the surface section 3.

The aforementioned surface section 3 is preferably formed on the fiber collection surface, and more preferably, formed on each of the collection surface and a section to contact the user's body. It is even more preferable that the surface section 3 on the fiber collection surface and the surface section 3 at the section to contact the user's body are formed continuously, and even more preferably, the surface section 3 is formed continuously over the entire region of the surface of the fiber collection tool 1. Forming the surface section 3 continuously over the entire region of the surface of the fiber collection tool 1 is advantageous, in that spinning and depositing of fiber can be performed even more easily, because there is no need to particularly take into consideration the orientation of the fiber collection tool 1 during electrospinning or the position in which the fiber collection tool 1 is held. In cases where the surface section 3 is formed continuously over the entire region of the surface of the fiber collection tool 1, it is preferable that the surface section 3 is formed by an electroconductive material satisfying the aforementioned conditions.

The electroconductive section 2 may be formed from a single material, or may be formed by using a plurality of materials in combination, so long as the effects of the present invention can be achieved. In cases where the electroconductive section 2 is formed by using a plurality of materials in combination, the materials may be mixed such that the boundary therebetween is clear or unclear, or may be arranged in layers. In this case, it is preferable that the materials constituting the electroconductive section 2 are electrically connected.

Similarly, the surface section 3 may be formed from a single material, or may be formed by using a plurality of materials in combination, so long as the effects of the present invention can be achieved. In cases where the surface section 3 is formed by using a plurality of materials in combination, the materials may be mixed such that the boundary therebetween is clear or unclear, or may be arranged in layers. The surface section 3 may be a combination of an electroconductive material and a non-electroconductive material, so long as the effects of the present invention can be achieved.

In cases where a surface section 3 is formed in the fiber collection tool 1, the surface electrical resistivity of the surface section 3 is preferably greater than $10^{11}$ Ω/cm², more preferably $1.1 \times 10^{11}$ Ω/cm² or greater, and is realistically $500 \times 10^{12}$ Ω/cm² or less from the viewpoint of securing electroconductivity of the entire fiber collection tool 1. By providing the surface section 3 with such surface electrical resistivity, spinning of fiber by electrospinning can be performed efficiently even in cases where the surface section 3 is formed on the fiber collection tool 1, and a fiber deposit can be formed in a desired position of the surface section 3. Such a surface section 3 can be formed, for example, by using the later-described material. The surface electrical resistivity of the surface section 3 may be the same at any discretionary position of the surface section 3, or may be different among various surface sections 3 within the aforementioned range of surface electrical resistivity.

The surface electrical resistivity can be measured, for example, according to the method of JIS K6911 (1995). More specifically, a measurement sample is obtained by cutting a surface section 3 of a fiber collection tool 1 being measured such that the surface in which the surface electrical resistivity is to be measured is 50 mm long and 45 mm wide, and the thickness is 4 mm. The measurement sample's surface to be measured is brought into contact with an inner electrode and a ring electrode of a Chamber R12704 from Advantest Corporation, so as to bridge the inner electrode and the ring electrode. In this state, using an electrical resistance meter R8340A from Advantest Corporation in Surface mode, a voltage is applied to the electrodes such that the potential difference between the chamber's electrodes becomes 500 V, and the resistivity ($\Omega/cm^2$) is measured. Measurement is performed in a temperature-humidity environment at room temperature of 22 to 23° C. and a relative humidity of 46%.

Examples of materials for forming the fiber collection tool 1 having the aforementioned configuration may include: solids, such as fiber sheets, metals, conductive carbon, elastic bodies, films, porous bodies, etc.; and fluids including liquids such as water, oil, etc., and gases such as air, etc. One type of the aforementioned material may be used singly, or a plurality of types may be used in combination, so long as the effects of the present invention can be achieved. The aforementioned three states—i.e., solid, liquid, and gas—are determined based on the state of a substance at 20° C.

As regards solid materials for forming the fiber collection tool 1, examples of fiber sheets may include various nonwoven fabrics, woven fabrics, knitted fabrics, paper, mesh sheets, and laminates thereof, made by using, as a raw material, a natural fiber such as pulp, cotton, hemp, silk, etc., or fiber containing a thermoplastic resin such as polyethylene, polypropylene, etc.

Examples of metals may include metal-made meshes and various sheets made by using, as a raw material, copper, aluminum, stainless steel, etc.

An example of conductive carbon may include graphite etc.

Examples of elastic bodies may include rubber-made meshes and various rubber sheets made by using, as a raw material, a rubber-like substance such as nitrile rubber, natural rubber, etc.

Examples of films may include mesh films and various film sheets made by using, as a raw material, resin such as polyethylene, polypropylene, etc.

Examples of porous bodies may include foams including, as a raw material, polyurethane, wet urethane, acrylonitrile•butadiene copolymer (NBR), styrenebutadiene copolymer (SBR), natural rubber (NR), ethylenepropylenediene copolymer (EPDM), melamine foam, polyvinyl alcohol (PVA), cellulose, etc.

The aforementioned materials may be used as is, or it may be possible to use a material obtained by subjecting at least a surface of the aforementioned material to a treatment for increasing electroconductivity, such as a hydrophilizing treatment or an electroconductive treatment, or to a treatment for reducing electroconductivity, such as a hydrophobizing treatment. Examples of treatments for increasing electroconductivity may include: mixing, coating or immersion of the aforementioned material with/in water, a surfactant, a salt, etc.; and mixing or coating of an electroconductive material such as copper, carbon, etc. Examples of treatments for reducing electroconductivity may include mixing, coating, etc., of the aforementioned material with a non-electroconductive material.

Examples of fluids for forming the fiber collection tool 1 may include: liquids such as water—e.g., ion-exchanged water, tap water (clean water), distilled water, ion-exchanged water, RO water, ultrapure water, etc.—silicone oils, vegetable oils, etc.; and gases such as air, helium gas, etc. A solid may be present in the fluid, so long as the effects of the present invention can be achieved.

In cases where the fiber collection tool 1 does not have the aforementioned surface section 3 or has a surface section 3 deformable by external force, it is preferable that the electroconductive section 2 constituting the fiber collection tool 1 is made from a material deformable by external force applied by the user's grip when the user grips the fiber collection tool 1. With this structure, the shape of the electroconductive section 2 can be deformed by application of gripping force, while maintaining excellent fiber spinnability. So, by changing the shape of the fiber collection surface, spinning can be performed so that the range for forming the fiber deposit and the planar shape thereof can take on a desired range and shape. The electroconductive section 2 may include, in combination, a plurality of molded bodies of materials deformable by external force, so long as the effects of the present invention can be achieved. In this case, it is preferable that the electroconductive sections 2 of the respective molded bodies are electrically connected.

Examples of the electroconductive section 2 made from a material deformable by external force may include one or more of the aforementioned solids such as the aforementioned fiber sheets, elastic bodies such as rubber, porous bodies, etc., liquids, gases, and matters including an electroconductive material obtained by subjecting these to a treatment for improving electroconductivity. In cases where the electroconductive section deforms by external force applied by the user's grip, the deformation of the material constituting the electroconductive section 2 may be plastic deformation or elastic deformation.

In cases where the fiber collection tool 1 is provided with a surface section 3, it is preferable that the surface section 3 is made from a material deformable by external force applied by the user's grip when the user grips the fiber collection tool 1, and more preferably includes an elastic material, and even more preferably is a monolithic molded body of the aforementioned material. With this structure, when the fiber deposit produced on the fiber collection tool 1 is to be applied onto an adhesion object, application can be achieved without harming the adhesion object. In addition, by using an elastic material, the fiber deposit can be pressed against the adhesion object, which can thus increase the area of contact between the fiber deposit and the adhesion object and improve the tight-adhesiveness of the fiber deposit. Examples of such materials may include one or more of solids, such as the aforementioned fiber sheets, rubber, porous bodies, etc., and matters including a non-electroconductive material obtained by subjecting these to a treatment for reducing electroconductivity. The surface section 3 may be a combination of a plurality of molded bodies of elastic material(s), so long as the effects of the present invention can be achieved.

Particularly, it is preferable that both the electroconductive section 2 and the surface section 3 are made from a material deformable by external force applied by the user's grip when the user grips the fiber collection tool 1. With this structure, the entire fiber collection tool 1 can deform by external force applied by the user's grip. As a result, the shape of the fiber collection tool 1 can be deformed easily by application of gripping force. So, by easily changing the shape of the fiber collection surface, spinning can be performed so that the range for forming the fiber deposit and the planar shape thereof can take on a desired range and shape. In addition, when the fiber deposit produced on the fiber collection tool 1 is to be applied onto an adhesion object, the area of contact between the fiber deposit and the adhesion object can be increased, thereby improving the tight-adhesiveness of the fiber deposit.

In cases where the fiber collection tool 1 includes an elastic material, the hardness of the material is preferably 1 or greater, more preferably 5 or greater, and preferably 95 or less, more preferably 90 or less, as measured with a rubber hardness meter. For example, the material hardness can be measured by: bringing a pressurizing surface of an indentor of a rubber hardness meter (ASKER Type FP) perpendicularly into contact with a side surface of a test piece; applying pressure for 3 seconds in this state; and reading the meter scale at that time.

In cases where the fiber collection tool 1 has a surface section 3, suitable combinations between materials for the electroconductive section 2 and the surface section 3 may be as described below, for example. The combination, however, can be varied as appropriate depending on, for example, the environment for performing electrospinning, the shape, area, etc. of the intended fiber deposit, and the like. More specifically, examples of suitable combinations between the material for the electroconductive section 2 and the material for the surface section 3 (electroconductive section's material/surface section's material) may include: metal/nonwoven fabric; ion-exchanged water/nitrile rubber; ion-exchanged water/nitrile rubber and woven fabric; ion-exchanged water/nitrile rubber and nonwoven fabric; ion-exchanged water/nitrile rubber and paper.

In cases where the fiber collection tool 1 has a surface section 3, suitable combinations of arrangements of the electroconductive section 2 and the surface section 3 may be as described below, for example. The combination, however, can be varied as appropriate depending on, for example, the environment for performing electrospinning, the shape, area, etc. of the intended fiber deposit, and the like. More specifically, examples may include: a configuration wherein a nonwoven fabric-made surface section 3 is formed on the surface of a metal-made electroconductive section 2; a configuration wherein a nitrile rubber-made surface section 3 is formed on the surface of an electroconductive section 2 constituted by ion-exchanged water; a configuration wherein nitrile rubber is provided on the surface of an electroconductive section 2 constituted by ion-exchanged water, and a woven fabric-made surface section 3 is formed on the surface of the rubber; a configuration wherein nitrile rubber is provided on the surface of an electroconductive section 2 constituted by ion-exchanged water, and a nonwoven fabric-made surface section 3 is formed on the surface of the rubber; and a configuration wherein nitrile rubber is provided on the surface of an electroconductive section 2 constituted by ion-exchanged water, and a paper-made surface section 3 is formed on the surface of the rubber.

The size of the electroconductive section 2 constituting the fiber collection tool 1 can be varied as appropriate depending on, for example, the material forming the electroconductive section 2 or the use of the fiber deposit formed by electrospinning, so long as it is of a size that allows a user to hold the fiber collection tool 1 with the hand. From the viewpoint of sufficiently securing electroconductivity of the fiber collection tool 1 during electrospinning and thereby further improving fiber spinnability, it is preferable that the volume of the electroconductive section 2 is preferably 200 cm$^3$ or greater, more preferably 300 cm$^3$ or greater, and preferably 2000 cm$^3$ or less, more preferably 1000 cm$^3$ or less.

In cases where the fiber collection tool 1 has a surface section 3, from the viewpoint of sufficiently securing electroconductivity of the fiber collection tool 1 during electrospinning and thereby further improving fiber spinnability, it is preferable that the thickness T1 of the surface section 3 is preferably 10 µm or greater, more preferably 50 µm or greater, and preferably 10$^4$ µm or less, more preferably 1000 µm or less. The thickness of the surface section 3 can be measured, for example, by using digital vernier calipers (QuantuMike from Mitutoyo Corporation) under no load. The thickness T1 of the surface section 3 may be the same at any discretionary position of the surface section 3, or may be different among various surface sections 3 within the aforementioned range of thickness.

In cases where at least one of the electroconductive section 2 or the surface section 3 constituting the fiber collection tool 1 includes a porous material, the structure of the porous material, such as the pores etc., may be as described in the explanation on the fiber collection tool having the aforementioned configuration (1).

The fiber collection tool 1 having the aforementioned configuration has a size that is holdable by the user's hand, and is thus easy to carry or take along. Also, the burden of gripping the tool during fiber spinning by electrospinning is reduced, thereby improving spinnability and spinning convenience. Further, the fiber collection tool 1 preferably has a surface electrical resistivity and/or volume electrical resistivity being equal to or less than a predetermined value, or includes an electroconductive section 2 in the interior of the fiber collection tool. This facilitates the formation of an electric field between an electrospinning device and the fiber collection tool 1, thereby offering excellent fiber spinnability by electrospinning. Furthermore, the user himself/herself can produce a desired film, and also, there is less limitation in terms of the areas where the film can be attached.

Next, with reference to FIGS. 3 and 4, a method for producing a deposit of fiber spun by electrospinning, and preferably a film constituted by the fiber deposit, will be described.

In the present production method, a fiber deposit F is produced by collecting, on a surface of a fiber collection tool 1, a fiber spun by a user A by performing electrospinning using an electrospinning device 10. The thus-produced fiber deposit F is preferably a film including the fiber deposit, more preferably a film consisting of the fiber deposit, and is preferably a porous film.

In the present production method, it is preferable that at least the fiber collection tool 1 has a size holdable by the user A's hand, and more preferably, both the fiber collection tool 1 and the electrospinning device 10 have a size holdable by the user A's hand. Thus, the tool/device is easy to carry or take along, and also, the burden of gripping during fiber spinning by electrospinning is reduced, thereby further improving spinning convenience. Furthermore, the user himself/herself can produce a desired film, and also, there is less restriction in terms of the areas where the film can be attached.

In the production method of the present invention, a film including a fiber deposit is produced on a surface of an object. More specifically, a film including a fiber deposit is produced on a surface of an object by transferring the formed film onto the surface of the object.

From the viewpoint of easily forming the film, it is preferable that the film constituted by the fiber deposit is formed by depositing fiber spun by electrospinning, and more preferably, formed by depositing the fiber on a surface of a fiber collection tool 1.

Figure 3:
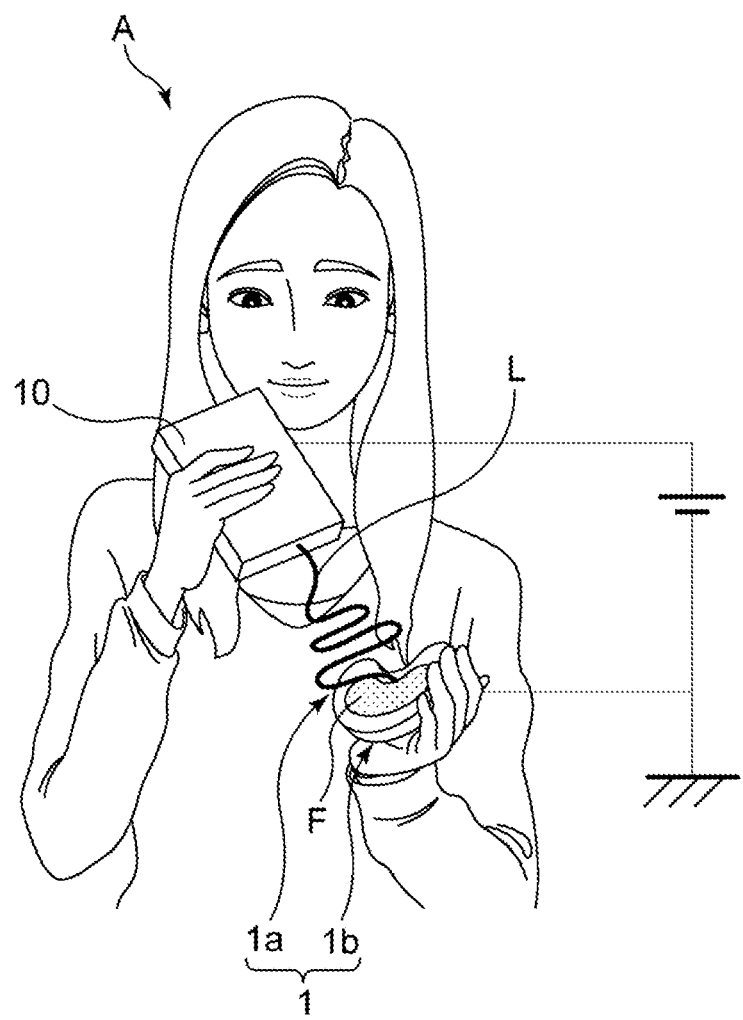
FIG. 3 is a schematic diagram illustrating an embodiment of a production method according to the present invention.

FIG. 3 illustrates an embodiment of a method for forming a film F on a surface of a fiber collection tool 1 by electrospinning. In the present method, a fiber spun by a user A by performing electrospinning using an electrospinning device 10 is collected with a fiber collection tool 1, and a film including a deposit of the fiber is formed on a surface of the fiber collection tool 1.

FIG. 3 illustrates an embodiment wherein, in a state where the user A, who is the producer of the fiber deposit F, holds the electrospinning device 10 with one hand and keeping a portion of the body, such as the other hand, in contact with the second principal surface 1b of the fiber collection tool 1, the user A himself/herself collects the fiber and produces the fiber deposit F. When producing the fiber deposit F, a power source (not illustrated) of the electrospinning device 10 is turned on in a state where a nozzle (not illustrated) of the electrospinning device 10, through which a material liquid L of the fiber is ejected, is facing the first principal surface 1a serving as the collection surface of the fiber collection tool 1. In this way, the material liquid is ejected from the nozzle in a state where the nozzle is applied with a positive or negative voltage, and thereby electrospinning is performed. In the embodiment illustrated in FIG. 3, electrospinning is performed in a state where a positive voltage is applied to the nozzle.

More specifically, when the power of the electrospinning device 10 is turned on, an electrical conduction path is formed between the nozzle of the electrospinning device 10 and the fiber collection tool 1, wherein the voltage of the nozzle is either positive or negative and the fiber collection tool 1 and the user's body in contact therewith are grounded. When the material liquid L is ejected from the electrospinning device 10 in this state, the electric field created between the nozzle and the fiber collection tool 1 causes the material liquid L, which is ejected into the electric field from the tip end of the nozzle, to polarize by electrostatic induction and thereby form a cone shape at the tip-end portion thereof. From the tip end of this cone, liquid droplets of the charged material liquid L are ejected into the air toward the fiber collection tool 1 along the electric field. The ejected material liquid L is repeatedly drawn by electric attraction and self-repellant force by the material liquid's own charge, and is thereby made into an ultrathin fiber, which reaches the first principal surface 1a serving as the collection surface. In this way, a fiber deposit F is formed on the collection surface. In cases where the fiber collection tool 1 has a surface section 3, the fiber deposit F is formed on the outermost surface of the surface section 3.

Particularly, by using a fiber collection tool 1 having the aforementioned volume electrical resistivity, or by using a fiber collection tool having a surface section 3 formed on the surface of the electroconductive section 2, the charged material liquid can easily be formed into a fiber and be deposited in a concentrated manner on a desired area of the collection surface, thus further improving fiber spinnability.

Figure 4:
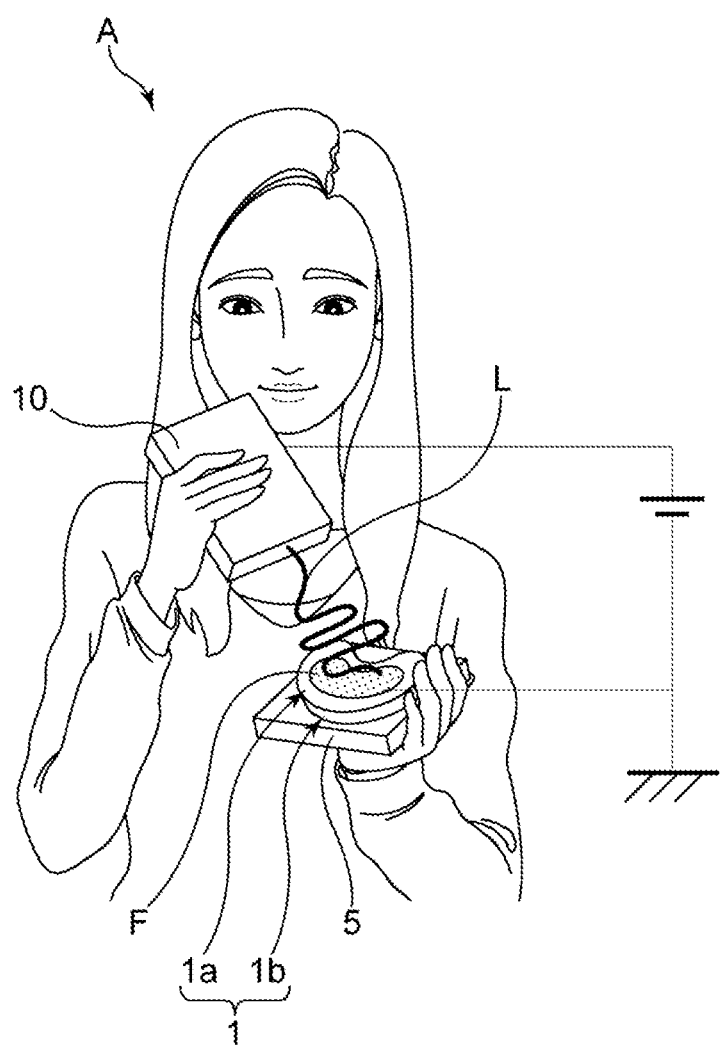
FIG. 4 is a schematic diagram illustrating another embodiment of a production method according to the present invention.

FIG. 4 illustrates another method for producing a fiber deposit F. In the embodiment illustrated in FIG. 4, the fiber collection tool 1 is placed on an electric conductor 5 such that the second principal surface 1b of the fiber collection tool 1 is in contact with the electric conductor 5. In this state, the user A performs electrospinning by holding the electrospinning device 10 with one hand and keeping a portion of the body, such as the other hand, in contact with the electric conductor 5. By performing electrospinning in this state, an electrical conduction path is formed, wherein the voltage of the nozzle is either positive or negative and the fiber collection tool 1, the electric conductor 5 and the user's body in contact therewith are grounded. The embodiment illustrated in FIG. 4 is in a state where a positive voltage is applied to the nozzle. As a result, as in the embodiment illustrated in FIG. 3, a fiber deposit F is formed on the first principal surface 1a serving as the collection surface.

The electric conductor 5 may be made from, for example, an electroconductive material such as metal etc. The planar-view shape of the electric conductor 5 is not particularly limited, so long as it has a surface on which the fiber collection tool 1 can be placed. Examples of the planar-view shape of the electric conductor 5 may include triangular, quadrangular, circular, elliptic, etc. The electric conductor 5 illustrated in FIG. 4 is a plate-like article having a rectangular planar-view shape. Like the fiber collection tool 1 and the electrospinning device 10, it is preferable that the electric conductor 5 has a size holdable by the user's hand.

In either of the aforementioned production methods, it is preferable that the fiber collection tool 1 to be used has one of the aforementioned configurations (1) to (3). That is, a fiber collection tool 1 having at least one of the aforementioned structures can preferably be used.

Further, in the fiber collection tool 1 to be used in the aforementioned production methods, it is preferable that the electroconductive section 2 is a material deformable by external force caused by gripping. It is also preferable that the surface section 3 has elasticity.

In the example of configuration (3), it is preferable that the fiber collection tool has a volume electrical resistivity of $10^{10}$ Ω·cm or less, and it is more preferable that a surface section 3 having a volume electrical resistivity different from the electroconductive section 2 is provided outside the electroconductive section 2, and it is further preferable that the surface electrical resistivity of the surface section 3 is greater than $10^{11}$ Ω/cm².

The electrospinning device 10 includes: a containing portion for containing a material liquid serving as a material for the fiber; an electroconductive nozzle for ejecting the material liquid; a power source for applying a voltage to the nozzle; and a housing for housing these elements therein. Any of various known types of devices may be used for the electrospinning device 10 having the aforementioned configuration, with usable examples including the electrostatic spraying device disclosed in JP 2017-078062A, the electrostatic spraying device disclosed in JP 2018-100301A, and the electrostatic spraying device disclosed in JP 2019-38856A.

According to the aforementioned method for producing a fiber deposit F (film F), the user A himself/herself operates the electrospinning device 10, and thus, it is possible to produce a film F having a shape and size as desired by the user A. Further, the film F is formed on the surface of the fiber collection tool 1, and thus, compared to methods wherein the film F is directly formed on the surface of a target object, it is possible to reliably transfer a desired film F onto the surface of an object and also transfer the film F even onto such parts as the eyes, nose, ears, neck, hair, etc., where it is difficult to perform electrospinning directly.

From the viewpoint of further improving handleability by the user A himself/herself at the time of forming a film F, it is preferable that one or both of the electrospinning device 10 and the fiber collection tool 1 have/has a size holdable by the user A's hand. In the method illustrated in FIG. 3, both the electrospinning device 10 and the fiber collection tool 1 have a size holdable by the user A's hand. Instead, either one of the electrospinning device 10 or the fiber collection tool 1 may have a size holdable by the user A's hand and the other may have a size that is not holdable by the user A's hand. For example, the electrospinning device may be a large stationary-type device.

The material liquid used for electrospinning is a solution or a melt of a polymer. The polymer used herein may have fiber formability, and concrete examples thereof may include water-soluble polymers and water-insoluble polymers. Herein, "water-soluble polymer" refers to a polymer having a property wherein, in an environment of 1 atm. and 23° C., when 1 g of the polymer is immersed in 10 g of ion-exchanged water, at least 0.5 g of the immersed polymer dissolves in water after 24 hours. On the other hand, herein, "water-insoluble polymer" refers to a polymer having a property wherein, in an environment of 1 atm. and 23° C., when 1 g of the polymer is immersed in 10 g of ion-exchanged water, less than 0.5 g of the immersed polymer dissolves in water after 24 hours. From the viewpoint of easily achieving fiber formability, it is preferable that the material liquid used for electrospinning contains a water-insoluble polymer.

Examples of the water-soluble polymer having fiber formability may include one or more types selected from: natural polymers, e.g., pullulan, mucopolysaccharides such as hyaluronic acid, chondroitin sulfate, poly-γ-glutamic acid, modified corn starch, β-glucan, glucooligosaccharide, heparin and keratosulfate, cellulose, pectin, xylan, lignin, glucomannan, galacturonic acid, psyllium seed gum, tamarind seed gum, gum arabic, tragacanth gum, water-soluble soybean polysaccharides, alginic acid, carrageenan, laminaran, agar (agarose), fucoidan, methyl cellulose, hydroxypropyl cellulose, and hydroxypropyl methylcellulose; and synthetic polymers, e.g., partially saponified polyvinyl alcohol (not used in combination with a cross-linking agent), low-saponification polyvinyl alcohol, polyvinyl pyrrolidone (PVP), polyethylene oxide, and sodium polyacrylate.

Among these water-soluble polymers, from the viewpoint of easy producibility of fibers, it is preferable to use one or more types selected from pullulan and synthetic polymers, such as partially saponified polyvinyl alcohol, low-saponification polyvinyl alcohol, polyvinyl pyrrolidone, polyethylene oxide, etc.

In cases of using polyethylene oxide as the water-soluble polymer, it is preferable that the number-average molecular weight thereof is preferably from 50,000 to 3,000,000, more preferably from 100,000 to 2,500,000.

Examples of the water-insoluble polymer having fiber formability may include one or more types selected from: completely saponified polyvinyl alcohol that can be made insoluble after formation of fibers, partially saponified polyvinyl alcohol that can be cross-linked after formation of fibers when used in combination with a cross-linking agent, oxazoline-modified silicone such as poly(N-propanoylethyleneimine)-graft-dimethylsiloxane/γ-aminopropylmethylsiloxane copolymer, polyvinylacetal diethylaminoacetate, zein (primary component of corn protein), polyester resins such as polylactic acid (PLA), polyacrylonitrile resins, acrylic resins such as polymethacrylate resins, polystyrene resins, polyvinyl butyral resins, polyethylene terephthalate resins, polybutylene terephthalate resins, polyurethane resins, polyamide resins, polyimide resins, and polyamide imide resins.

Among these water-insoluble polymers, it is preferable to use one or more types selected from completely saponified polyvinyl alcohol that can be made insoluble after formation of a film constituted by a fiber deposit, partially saponified polyvinyl alcohol that can be cross-linked after formation of a film constituted by a fiber deposit when used in combination with a cross-linking agent, polyvinyl butyral resins, acrylic resins such as (alkyl acrylateoctylamide) copolymer etc., oxazoline-modified silicone such as poly(N-propanoylethyleneimine)-graft-dimethylsiloxane/γ-aminopropylmethylsiloxane copolymer, polyurethane resins, polyester resins such as polylactic acid, and zein.

In cases of using a solution containing the aforementioned polymer as the material liquid used for electrospinning, examples of solvents usable for the polymer solution may include one or more types selected from volatile substances such as alcohols, e.g., ethanol, isopropyl alcohol, butyl alcohol, etc., and water.

In this production method, from the viewpoint of successfully forming a fiber deposit in a predetermined position, the shortest distance between the tip end of the nozzle of the electrospinning device 10 and the collection surface of the fiber collection tool 1 may preferably be 30 mm or greater, more preferably 50 mm or greater, even more preferably 80 mm or greater, and preferably 180 mm or less, more preferably 150 mm or less.

From the viewpoint of further improving the transferring properties of the fiber deposit (film), it is preferable that a film F having a higher adhesiveness to the object than the adhesiveness to the fiber collection tool 1 is formed on the surface of the fiber collection tool. From the viewpoint of making the adhesiveness between the fiber deposit (film) and the object higher than the adhesiveness between the film F and the fiber collection tool 1, it is preferable to perform a treatment that reduces the adhesiveness between the film F and the fiber collection tool 1. Examples of such treatments may include coating or spraying the surface of the fiber collection tool 1 with the aforementioned agent having a releasing action, providing the surface of the fiber collection tool 1 with a projecting-and-depressed structure, coating the surface of the object with an adhesive, and the like.

The fiber deposit F produced through the aforementioned steps is preferably a porous film-like product constituted by a deposit of fiber. Such a fiber deposit F can be used by being attached onto the surface of an adhesion object. Examples of objects to which the deposit can be attached may include the skin, nails, teeth, gums or hair of a human being, the skin, teeth or gums of a non-human mammal, and the surface of a plant such as the branches or leaves, and may preferably be the skin or nails of a human being. Particularly, the fiber deposit obtained by the present invention can suitably be used for various aesthetic methods that are not intended for surgical, therapeutic or diagnostic methods for the human body. More specifically, the fiber deposit may be used for aesthetic purposes, such as whitening of the skin in the applied areas, concealing of spots on the skin, concealing of dullness/dark circles on the skin, concealing of wrinkles on the skin, blurring of the skin, protection of the skin from UV rays, moisturizing of the skin, and the like. Other than the above, the fiber deposit may be used for various actions conducted domestically and personally for the protection of the skin, such as protection of various wounds, e.g., abrasion, cuts, laceration, stab wounds, etc., prevention of bedsores, and the like.

In cases where electrospinning is employed to form a film F constituted by a fiber deposit, it is possible to obtain a film F whose thickness gradually decreases from the film's central section toward the film's outer edge. Also, the film F will be formed by electrospinning by the user A's operation.

Stated differently, the film F will be formed in a shape and size as desired by the user A, and thus, there is no need for cutting.

Further, before being transferred onto the object, the film F formed on the surface of the fiber collection tool 1 may be subjected to such a process as vapor deposition, plating, printing, etc. In such cases, for example, the process is performed in a state where the film F is arranged on the surface of the fiber collection tool 1. In this way, the film F can be subjected to a process that would otherwise be difficult to apply directly onto an object such as the skin, and by transferring the processed film F onto the object, a finish can be obtained as if the process were directly applied to the object. More specifically, for example, a film F on the surface of the fiber collection tool 1 may be subjected to a printing process for printing a predetermined design/pattern, and by transferring the processed film F onto an object, a finish can be obtained as if the design/pattern were directly rendered on the object. The more elaborate the design/pattern is, the better the working efficiency, compared to methods of directly rendering the design/pattern onto the object.

For the printing process, it is possible to use a known printing method such as inkjet printing, etc., and it is also possible to use printing methods that are difficult to apply directly to an object. For example, a printing process involving vapor deposition, UV curing or heat treatment of an ink material is difficult to apply to the skin. However, by applying this printing process to the film F and then transferring the film onto the skin, a finish employing this printing process can be obtained.

Figure 5A:
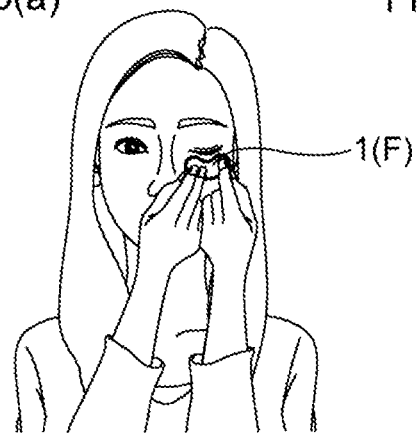
FIGS. 5(a) and 5(b) are schematic diagrams illustrating an embodiment of a method for attaching a deposit (film) of fiber.
Figure 5B:
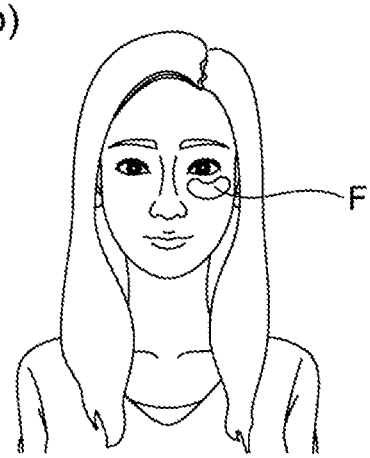

FIGS. 5(a) and 5(b) illustrate an embodiment wherein a fiber deposit F formed on the surface of a fiber collection tool 1 is applied to the skin near a person's eye, serving as an object to which the film is attached. Stated differently, the present embodiment is an embodiment of a method for attaching a film.

In the present mode of use, as illustrated in FIG. 5(a), a fiber deposit F formed on the surface of a fiber collection tool 1 is brought in opposition to the surface of the skin, serving as an adhesion object, and the fiber deposit F is then pressed against or otherwise brought into contact with the surface of the skin and is attached thereto. Then, the fiber collection tool 1 is separated and removed from the adhesion object such that the fiber deposit F is peeled off from the surface of the fiber collection tool 1. In this way, as illustrated in FIG. 5(b), only the fiber deposit F adheres to the surface of the adhesion object. That is, the film F is transferred onto the surface of the object.

Particularly, from the viewpoint of improving the tight-adhesiveness between the fiber deposit F and the surface of the adhesion object and also improving the appearance of the area where the fiber deposit has been attached, it is preferable to attach the fiber deposit F in a moistened state onto the surface of the adhesion object. Examples of methods therefor may include: (i) a method of making the fiber deposit F adhere to the object's surface in a state where the object's surface is moistened; (ii) a method of moistening the fiber deposit F after making the fiber deposit F adhere to the object's surface; and (iii) a method of making the fiber deposit F adhere to the object's surface in a state where the fiber deposit F is moistened. To bring the fiber deposit F in a moistened state, a liquid substance, including various aqueous liquids, may be applied to the fiber deposit F and/or the surface of the adhesion object by coating, spraying, etc.

In cases where the aforementioned liquid substance contains water, examples of the liquid substance may be a liquid, such as water, an aqueous solution, an aqueous dispersion, etc., a gel-like substance thickened with a thickener, an oil that is either liquid or solid at 20° C., an oily agent containing 10 mass % or greater of the aforementioned oil, an emulsion (O/W emulsion or W/O emulsion) containing the aforementioned oil and a surfactant such as a nonionic surfactant, or the like.

In cases where the aforementioned liquid substance contains a polyol that is liquid at 20° C., examples of the polyol may include one or more types selected from ethylene glycol, propylene glycol, 1,3-butanediol, dipropylene glycol, polyethylene glycol having a weight-average molecular weight of 2000 or less, glycerin, and diglycerin.

In cases where the aforementioned liquid substance contains an oil that is liquid at 20° C., examples of the oil may include: one or more types of hydrocarbon oils selected from liquid paraffin, squalane, squalene, n-octane, n-heptane, cyclohexane, light isoparaffin and liquid isoparaffin; one or more types of ester oils selected from esters of linear or branched fatty acids and linear or branched alcohols or polyols, such as octyldodecyl myristate, myristyl myristate, isocetyl stearate, isocetyl isostearate, cetearyl isononanoate, diisobutyl adipate, di-2-ethylhexyl sebacate, isopropyl myristate, isopropyl palmitate, diisostearyl malate, neopentyl glycol dicaprate and alkyl (C12-15) benzoate, and triglycerol fatty acid esters (triglycerides) such as caprylic/capric triglyceride; and one or more types of silicone oils selected from dimethyl polysiloxane, dimethyl cyclopolysiloxane, methylphenyl polysiloxane, methylhydrogen polysiloxane and higher alcohol-modified organopolysiloxane. The aforementioned oil may be used singly, or two or more types may be used in combination.

In cases where the aforementioned liquid substance contains a fat that is solid at 20° C., examples of the fat may include one or more types selected from vaseline, cetanol, stearyl alcohol, and ceramide.

From the viewpoint of further improving transferring properties, it is preferable to apply in advance, to the surface of the object, an agent for increasing adhesiveness between the object and the film F, and in this state, press the fiber collection tool 1, having the film F formed thereon, against the surface of the object. The agent for increasing adhesiveness is applied to the object by being coated or sprayed onto the surface of the object.

For the agent for increasing adhesiveness, any agent capable of increasing the adhesiveness between an object and the film F can be used without particular limitation, with examples including liquid cosmetics such as toners, moisturizers, creams, gels, serums, etc.

The present invention has been described above according to preferred embodiments thereof, but the present invention is not limited to the foregoing embodiments. For example, in the embodiment illustrated in FIG. 3, the user holds both the fiber collection tool 1 and the electrospinning device 10 and creates an electric field between the fiber collection tool 1 and the nozzle of the electrospinning device 10. However, the user himself/herself does not necessarily have to hold both the fiber collection tool 1 and the electrospinning device 10, so long as an electric field can be created therebetween.

Further, in the embodiments illustrated in FIGS. 3 and 4, the electrospinning device 10 has a size holdable with the hand, but instead, the electrospinning device may be a large stationary-type device.

Further, in the embodiments illustrated in FIGS. 3 and 4, the fiber is deposited directly on the collection surface of the fiber collection tool 1, but so long as the effects of the present invention can be achieved, a fiber sheet, such as a nonwoven fabric, may be further arranged on the collection surface and spinning of fiber may be performed in this state, to form a film including the fiber deposit on the fiber sheet.

Further, the embodiments illustrated in FIGS. 3 and 4 describe examples wherein electrospinning is performed with the fiber collection tool 1 being directly held with the hand or the fiber collection tool 1 being held with the hand via the electric conductor 5. However, so long as the effects of the present invention can be achieved, electrospinning may be performed in a state where the fiber collection tool 1 is in contact, either directly or via the electric conductor 5, with a portion of the user's body other than the hand. Examples of body parts other than the user's hand may include the arm, leg, elbow, knee, etc., although not limited thereto.

In relation to the foregoing embodiments, the present invention further discloses the following fiber collection tools, fiber deposit production methods using the same, film production methods, and film attachment methods.

{1}
A fiber collection tool to be used for collecting a fiber spun by electrospinning, wherein:
the fiber collection tool has a size holdable by a user's hand, and includes, in its interior, an electroconductive section.

{2}
The fiber collection tool as set forth in clause {1}, wherein the volume electrical resistivity is preferably $10^{10}$ Ω·cm or less, more preferably $5 \times 10^9$ Ω·cm or less, even more preferably $10^9$ Ω·cm or less.

{3}
The fiber collection tool as set forth in clause {1} or {2}, wherein the volume electrical resistivity is preferably $10^0$ Ω·cm or greater.

{4}
The fiber collection tool as set forth in any one of clauses {1} to {3}, further including a surface section outside the electroconductive section, wherein:
the volume electrical resistivity of the surface section is greater than the volume electrical resistivity of the electroconductive section.

{5}
The fiber collection tool as set forth in clause {4}, wherein the surface electrical resistivity of the surface section is preferably greater than $10^{11}$ Ω/cm², more preferably $1.1 \times 10^{11}$ Ω/cm² or greater.

{6}
The fiber collection tool as set forth in clause {4} or {5}, wherein the surface electrical resistivity of the surface section is preferably $500 \times 10^{12}$ Ω/cm² or less.

{7}
The fiber collection tool as set forth in any one of clauses {4} to {6}, wherein the fiber collection surface and a section to contact the user's body each have the surface section.

{8}
The fiber collection tool as set forth in any one of clauses {4} to {7}, wherein the surface section of the fiber collection surface and the surface section of the section to contact the user's body are formed continuously.

{9}
The fiber collection tool as set forth in any one of clauses {4} to {8}, wherein the surface section is formed continuously over the entire region of the surface of the fiber collection tool.

{10}
The fiber collection tool as set forth in any one of clauses {4} to {9}, wherein the surface section
is preferably made from a material deformable by external force applied by the user's grip when the user grips the fiber collection tool,
more preferably includes an elastic material, and
is even more preferably a monolithic molded body of the aforementioned material.

{11}
The fiber collection tool as set forth in any one of clauses {4} to {10}, wherein both the electroconductive section and the surface section are made from a material deformable by external force applied by the user's grip when the user grips the fiber collection tool.

{12}
The fiber collection tool as set forth in any one of clauses {4} to {11}, wherein a combination between the material for the electroconductive section and the material for the surface section (electroconductive section's material/surface section's material) is at least one selected from: metal/nonwoven fabric; ion-exchanged water/nitrile rubber; ion-exchanged water/nitrile rubber and woven fabric; ion-exchanged water/nitrile rubber and nonwoven fabric; and ion-exchanged water/nitrile rubber and paper.

{13}
The fiber collection tool as set forth in any one of clauses {1} to {12}, wherein:
the mass of the fiber collection tool is preferably 500 g or less, more preferably 200 g or less;
the maximum length spanning the fiber collection tool is preferably from 0.1 mm to 30 cm; and
the volume of the fiber collection tool is preferably from 0.5 cm³ to $10^4$ cm³.

{14}
A method for producing a fiber deposit, comprising:
collecting a fiber with a fiber collection tool, the fiber being spun by a user by performing electrospinning using an electrospinning device; and
producing a deposit of the fiber on a surface of the fiber collection tool, wherein:
the fiber collection tool includes, in its interior, an electroconductive section.

{15}
The method for producing a fiber deposit as set forth in clause {14}, wherein electrospinning is performed in a state where the user holds the electrospinning device with one hand and holds the fiber collection tool with the other hand, and an electrical conduction path passing through the user's body is formed between the electrospinning device and the fiber collection tool.

{16}
The method for producing a fiber deposit as set forth in clause {14}, wherein electrospinning is performed in a state where the user holds the electrospinning device with one hand and holds an electric conductor with the other hand with the electric conductor in contact with the fiber collection tool, and an electrical conduction path passing through the user's body and the electric conductor is formed between the electrospinning device and the fiber collection tool.

{17}
The method for producing a fiber deposit as set forth in any one of clauses {14} to {16}, wherein the fiber collection tool has a volume electrical resistivity of $10^{10}$ Ω·cm or less.

{18}
The method for producing a fiber deposit as set forth in any one of clauses {14} to {17}, wherein:
- the fiber collection tool further includes a surface section outside the electroconductive section; and
- the surface section has a surface electrical resistivity of greater than $10^{11}$ Ω/cm$^2$.

{19}
The method for producing a fiber deposit as set forth in any one of clauses {14} to {18}, wherein:
- the electrospinning is performed by using a material liquid serving as a material for the fiber; and
- the material liquid is a solution or a melt containing a polymer having fiber formability.

{20}
The method for producing a fiber deposit as set forth in clause {19}, wherein:
- the polymer having fiber formability includes a water-soluble polymer; and
- the water-soluble polymer is preferably one or more types selected from: natural polymers, including pullulan, mucopolysaccharides such as hyaluronic acid, chondroitin sulfate, poly-γ-glutamic acid, modified corn starch, β-glucan, glucooligosaccharide, heparin and keratosulfate, cellulose, pectin, xylan, lignin, glucomannan, galacturonic acid, psyllium seed gum, tamarind seed gum, gum arabic, tragacanth gum, water-soluble soybean polysaccharides, alginic acid, carrageenan, laminaran, agar (agarose), fucoidan, methyl cellulose, hydroxypropyl cellulose, and hydroxypropyl methylcellulose; and synthetic polymers, including partially saponified polyvinyl alcohol (not used in combination with a cross-linking agent), low-saponification polyvinyl alcohol, polyvinyl pyrrolidone (PVP), polyethylene oxide, and sodium polyacrylate.

{21}
The method for producing a fiber deposit as set forth in clause {19}, wherein:
- the polymer having fiber formability includes a water-insoluble polymer; and
- the water-insoluble polymer is preferably one or more types selected from completely saponified polyvinyl alcohol that can be made insoluble after formation of fibers, partially saponified polyvinyl alcohol that can be cross-linked after formation of fibers when used in combination with a cross-linking agent, oxazoline-modified silicone such as poly(N-propanoylethyleneimine)-graft-dimethylsiloxane/γ-aminopropylmethylsiloxane copolymer, polyvinylacetal diethylaminoacetate, zein (primary component of corn protein), polyester resins such as polylactic acid (PLA), polyacrylonitrile resins, acrylic resins such as polymethacrylate resins, polystyrene resins, polyvinyl butyral resins, polyethylene terephthalate resins, polybutylene terephthalate resins, polyurethane resins, polyamide resins, polyimide resins, and polyamide imide resins.

{22}
The method for producing a fiber deposit as set forth in clause {21}, wherein the water-insoluble polymer is one or more types selected from completely saponified polyvinyl alcohol that can be made insoluble after formation of a film constituted by a fiber deposit, partially saponified polyvinyl alcohol that can be cross-linked after formation of a film constituted by a fiber deposit when used in combination with a cross-linking agent, polyvinyl butyral resins, acrylic resins such as (alkyl acrylate•octylamide) copolymer, oxazoline-modified silicone such as poly(N-propanoylethyleneimine)-graft-dimethylsiloxane/γ-aminopropylmethylsiloxane copolymer, polyurethane resins, polyester resins such as polylactic acid, and zein.

{23}
The method for producing a fiber deposit as set forth in any one of clauses {19} to {22}, wherein:
- a solution containing a polymer having fiber formability is used as the material liquid; and
- a solvent usable for the solution is one or more types selected from volatile substances such as alcohols, e.g., ethanol, isopropyl alcohol and butyl alcohol, and water.

{24}
The method for producing a fiber deposit as set forth in any one of clauses {14} to {23}, wherein:
- the electrospinning device includes a containing portion for containing a material liquid serving as a material for the fiber, an electroconductive nozzle for ejecting the material liquid, a power source for applying a voltage to the nozzle, and a housing for housing these elements therein; and
- the shortest distance between the tip end of the nozzle and the collection surface of the fiber collection tool is preferably 30 mm or greater, more preferably 50 mm or greater, even more preferably 80 mm or greater, and preferably 180 mm or less, more preferably 150 mm or less.

{25}
A method for producing a film on a surface of an object, the film comprising a fiber deposit,
the method comprising:
- forming, by the method as set forth in any one of claims 1 to 7, a film including a deposit of the fiber on a surface of the fiber collection tool, the forming being performed by a user; and
- pressing the fiber collection tool, which has the film formed thereon, against a surface of an object and transferring the film onto the surface of the object, to form the film including the fiber deposit on the surface of the object.

{26}
The method for producing a film as set forth in clause {25}, wherein:
- one or both of the electrospinning device and the fiber collection tool has/have a size holdable by the user's hand;
- the user collects the fiber with the fiber collection tool, and forms the film including the fiber deposit on the surface of the fiber collection tool; and
- the user presses the fiber collection tool, having the film formed thereon, against the surface of the object.

{27}
The method for producing a film as set forth in clause {25} or {26}, wherein:
- the mass of the fiber collection tool is 500 g or less, preferably 200 g or less; and
- the maximum length spanning the fiber collection tool is from 0.1 mm to 30 cm.

{28}
The method for producing a film as set forth in any one of clauses {25} to {27}, wherein:
- the mass of the electrospinning device is 3000 g or less, preferably 2000 g or less; and
- the maximum length spanning the electrospinning device is 40 cm or less.

{29}

The method for producing a film as set forth in any one of clauses {25} to {28}, wherein the fiber collection tool has, in the surface thereof, one or a plurality of depressions.

{30}

The method as set forth in clause {29}, wherein the depressions are through holes, penetrating grooves, or micropores in a porous body.

{31}

The method for producing a film as set forth in clause {30}, wherein the porous body is a foam including, as a material, at least one type selected from polyurethane, wet urethane, acrylonitrile•butadiene copolymer (NBR), styrenebutadiene copolymer (SBR), natural rubber (NR), ethylenepropylenediene copolymer (EPDM), melamine foam, polyvinyl alcohol (PVA), and cellulose.

{32}

The method for producing a film as set forth in any one of clauses {25} to {31}, wherein the fiber collection tool has, on the surface thereof, a section including napped fiber.

{33}

The method for producing a film as set forth in clause {32}, wherein the napped section is a section in which short fibers are fixed on the surface in a standing state.

{34}

The method for producing a film as set forth in any one of clauses {25} to {33}, wherein the fiber collection tool has, on the surface thereof, an agent having an action of releasing the film.

{35}

The method for producing a film as set forth in clause {34}, wherein the agent having a releasing action is preferably a powdery agent, and more preferably is at least one type selected from silicic acid, silicic acid anhydride, magnesium silicate, talc, sericite, mica, kaoline, colcothar, clay, bentonite, mica, titanium-coated mica, bismuth oxychloride, zirconium oxide, magnesium oxide, titanium oxide, zinc oxide, aluminum oxide, calcium sulfate, barium sulfate, magnesium sulfate, calcium carbonate, magnesium carbonate, iron oxide, ultramarine blue, chromium oxide, chromium hydroxide, calamine, carbon black, boron nitride, polyamide, nylon, polyester, polypropylene, polystyrene, polyurethane, vinyl resins, urea resins, phenolic resins, fluorocarbon resins, silicon resins, acrylic resins, melamine resins, epoxy resins, polycarbonate resins, divinylbenzene•styrene copolymer, silk powder, cellulose, metal salts of long-chain alkyl phosphates, N-mono-long-chain alkyl acyl basic amino acids, and composites of the above.

{36}

The method for producing a film as set forth in any one of clauses {25} to {35}, comprising:

applying in advance, to the surface of the object, an agent for increasing adhesiveness between the object and the film, and in this state, pressing the fiber collection tool, having the film formed thereon, against the surface of the object.

{37}

The method for producing a film as set forth in clause {36}, wherein the agent for increasing adhesiveness is at least one type of liquid cosmetic selected from toners, moisturizers, creams, gels, and serums.

{38}

The method for producing a film as set forth in any one of clauses {25} to {37}, wherein the film formed on the surface of the fiber collection tool has a higher adhesiveness to the object than the adhesiveness to the fiber collection tool.

{39}

The method as set forth in any one of clauses {25} to {38}, wherein the thickness of the film gradually decreases from the film's central section toward the film's outer edge.

{40}

The method for producing a film as set forth in any one of clauses {25} to {39}, wherein, before being transferred onto the object, the film formed on the surface of the fiber collection tool is subjected to at least one process selected from vapor deposition, plating, and printing.

{41}

The method for producing a film as set forth in clause {40}, wherein the process is printing, and preferably inkjet printing.

{42}

A method for attaching a film, comprising:

collecting, with a fiber collection tool, a fiber spun by a user by performing electrospinning using an electrospinning device, and forming a film including a deposit of the fiber on a surface of the fiber collection tool; and pressing the fiber collection tool, having the film formed thereon, against a surface of an object and attaching the film onto the surface of the object.

EXAMPLES

The present invention will be described in further detail below according to Examples. Note, however, that the scope of the present invention is not limited to the following Examples.

Example 1-1

For the fiber collection tool 1, an electroconductive section 2 consisting of 200 mL of ion-exchanged water was housed inside a nitrile rubber-made bag having a thickness of 60 μm, to form a surface section 3 made from nitrile rubber. The fiber collection tool 1 of the present Example had a structure wherein the nitrile rubber-made surface section 3 was arranged directly outside the electroconductive section 2 as illustrated in FIG. 2, and had a substantially ellipsoidal three-dimensional shape. In the fiber collection tool 1 of the present Example, the electroconductive section 2 was formed in the entire interior of the fiber collection tool 1, the surface section 3 was formed over the entire surface of the fiber collection tool 1, and the entire fiber collection tool 1 was constructed so as to be deformable by external force. The surface electrical resistivity of the surface section 3 was substantially the same in all areas (mass: 210 g; maximum major-axis length: 150 mm).

The fiber collection tool 1 was placed on the user's palm such that a portion of the surface of the fiber collection tool was in contact with the palm of one of the user's hands, and the user held an electrospinning device 10 with the other hand, and in this state, electrospinning was performed with the nozzle facing the outer surface of the fiber collection tool 1, to thereby form a porous film-like fiber deposit F on the surface of the fiber collection tool 1. The spinning conditions were as follows.

Spinning Conditions:
Spinning environment: 25° C., 50% RH
Material liquid for electrospinning Mixed solution of polyvinyl butyral resin (12 mass %; S-LEC B BM-1 (product name) from Sekisui Chemical Co., Ltd.) and 99.5% ethanol (88 mass %).
Voltage applied to nozzle: 14.5 kV
Distance between nozzle and fiber collection tool 1: 80 mm
Material liquid ejection rate: 7.2 mL/h
Nozzle diameter: 0.7 mm Example 1-2

An article made by forming a surface section 3 by further covering the entire outer surface of the fiber collection tool of Example 1-1 with a 1300-μm-thick woven fabric made from cotton fiber was used as the fiber collection tool 1. More specifically, the fiber collection tool 1 of the present Example had a surface section 3, including a nitrile rubber-made inner layer and a woven fabric-made outer layer, formed on the surface of an electroconductive section 2 consisting of ion-exchanged water, with the woven fabric constituting the outermost surface of the fiber collection tool 1. The electroconductive section 2 and the surface section 3 were electrically connected. The fiber collection tool 1 of the present Example had a substantially ellipsoidal three-dimensional shape. Other than the above, electrospinning was performed as in Example 1-1, to form a porous fiber deposit F on the surface of the fiber collection tool 1 (mass: 240 g; maximum major-axis length: 150 mm).

Examples 1-3 and 1-4

In the respective fiber collection tools 1 used in each of these Examples, the surface section 3 was formed by covering the tool with either a 300-μm-thick nonwoven fabric made from rayon fiber (Example 1-3) or 230-μm-thick paper (Example 1-4; Kim Towel from Nippon Paper), instead of the fiber sheet of Example 1-2. Other than the above, electrospinning was performed as in Example 1-1, to form a porous fiber deposit F on the surface of the respective fiber collection tool 1. More specifically, the respective fiber collection tools 1 of the present Examples each had a surface section 3, including a nitrile rubber-made inner layer and an outer layer consisting of either nonwoven fabric or paper, formed on the surface of an electroconductive section 2 consisting of ion-exchanged water, with either the nonwoven fabric or paper constituting the outermost surface of the fiber collection tool 1 (each having a mass of 240 g and a maximum major-axis length of 150 mm).

Comparative Example 1-1

Electrospinning was performed as in Example 1-1 to form a porous fiber deposit F on the surface of the fiber collection tool 1, except that the fiber collection tool 1 used herein contained air as the electroconductive section 2 instead of water (mass: 10 g; maximum major-axis length: 150 mm).

Comparative Example 1-2

Electrospinning was performed as in Example 1-1 to form a porous fiber deposit F on the surface of the fiber collection tool 1, except that that the fiber collection tool 1 used herein contained 200 mL of silicone oil (KF-96-10cs from Shin-Etsu Chemical Co., Ltd.) as the electroconductive section 2 instead of water (mass: 200 g; maximum major-axis length: 150 mm).

Measurement of Volume Electrical Resistivity and Surface Electrical Resistivity:
The volume electrical resistivity and surface electrical resistivity of each of the fiber collection tools used in the Examples and Comparative Examples were measured according to the aforementioned methods. The results are shown in Table 1.

Evaluation of Spinnability:
The respective fiber collection tools of the Examples and Comparative Examples were used, and fiber was electrospun for 5 seconds toward the centroid of the collection surface of the fiber collection tool, to obtain a porous film constituted by a fiber deposit F having a circular planar-view shape. The diameter of each porous film was measured, and the spinnability of the formed fiber was evaluated according to the following criteria. The results are shown in Table 1.

Criteria for Evaluating Spinnability:
A: Very good targeting properties; it was possible to electrospin fiber efficiently, and the diameter of the obtained fiber deposit was 2 cm or less.
B: Good targeting properties; electrospinning of fiber was possible, and the diameter of the obtained fiber deposit was greater than 2 cm to 4 cm or less.
C: Poor targeting properties; although electrospinning of fiber was possible, the diameter of the obtained fiber deposit was greater than 4 cm.

TABLE 1

| | | | Example 1-1 | Example 1-2 | Example 1-3 | Example 1-4 | Comp. Example 1-1 | Comp. Example 1-2 |
|---|---|---|---|---|---|---|---|---|
| Fiber collection tool | Electro-conductive section | Material(s) | Water | Water | Water | Water | Air | Silicone oil |
| | Surface section | Material(s) | Nitrile rubber | Inner layer: Nitrile rubber Outer layer: Cotton woven fabric | Inner layer: Nitrile rubber Outer layer: Nonwoven fabric | Inner layer: Nitrile rubber Outer layer: Paper | Nitrile rubber | Nitrile rubber |
| | | Surface electrical resistivity ($\times 10^{12}$ $\Omega/cm^2$) | 0.11 | 290 | 38 | 0.01 | 0.11 | 0.11 |
| | | Volume electrical resistivity ($\times 10^9$ $\Omega \cdot cm$) | 0.88 | 1.9 | 3.5 | 1.6 | 29 | 26 |
| Diameter of fiber deposit (cm) | | | 2 | 3 | 4 | 3 | 5 | 6 |
| Evaluation of spinnability | | | A | B | B | B | C | C |

Table 1 shows that, compared to the fiber collection tools of the Comparative Examples, the fiber collection tools of the Examples are superior in fiber spinnability, and are also superior in electrospinning targeting properties, as fiber deposits with a predetermined shape can be formed easily in a predetermined position.

Example 2-1

A cosmetic sponge (product name "Yukilon Grace MG") from Yukigaya Chemical Industry Co., Ltd. was prepared as the fiber collection tool 1. This fiber collection tool was an elastic molded body, constituted by a NBR-made porous body and having a pair of 60-mm-long, 65-mm-wide rectangular principal surfaces and 15-mm-thick side surfaces. The fiber collection tool had a plurality of pores including closed pores and open pores, and pores having pore diameters within a range of around 40 µm to 300 µm were present in a combined manner. The apparent density of the porous body was 0.155 g/cm$^3$, and the hardness of the porous body measured according to the aforementioned method was 26.4. The fiber collection tool of the present Example had a plurality of depressions over its entire surface.

The fiber collection tool 1 was placed on the user's palm such that one of the fiber collection tool's principal surfaces was in contact with the palm of one of the user's hands, and the user held an electrospinning device 10 with the other hand, and in this state, electrospinning was performed with the nozzle facing the other principal surface of the fiber collection tool 1, to thereby form, on the surface of the fiber collection tool 1, a porous circular film F having a diameter of about 3 cm. The spinning conditions were as follows.

Spinning Conditions:
Spinning environment: 25° C., 50% RH
Material liquid for electrospinning Mixed solution of polyvinyl butyral resin (12 mass %; S-LEC B BM-1 (product name) from Sekisui Chemical Co., Ltd.) and 99.5% ethanol (88 mass %)
Voltage applied to nozzle: 14.5 kV
Distance between nozzle and fiber collection tool 1: 80 mm
Material liquid ejection rate: 7.2 mL/h
Nozzle diameter: 0.7 mm
Spinning time: 5 seconds
After forming the film F, the user pressed the fiber collection tool 1, having the film F formed thereon, against his/her cheek, to thereby transfer the film F onto the cheek.

Example 2-2

A film F was formed and the film was transferred onto the user's cheek as in Example 2-1, except that, for the fiber collection tool 1, a cosmetic puff (product name "Puff for Face Powder") from Tokyo Puff Co., Ltd. was used. This fiber collection tool was an elastic molded body, constituted by a polyester-made porous body having a pair of 90-mm-dia. circular principal surfaces and a 15-mm-thick side surface. The fiber collection tool of the present Example had a napped section over the entire surface of the porous body, and the hardness measured according to the aforementioned method was 17.

Example 2-3

A film F was formed and the film was transferred onto the user's cheek as in Example 2-1, except that, for the fiber collection tool 1, a rubber container (product name "Clean Knoll Nitrile Short Gloves") from AS ONE Corporation was used, and an agent having a film-releasing action was applied to the fiber collection tool 1. The rubber container was a product ordinarily used as a glove. The interior of the glove was filled with 200 mL of water from the opening for inserting the hand and the glove was sealed in this state, to produce a fiber collection tool having an electroconductive section in its interior. This fiber collection tool was a nitrile-made elastic molded body having a pair of 75-mm-dia. circular principal surfaces and a 50-mm-thick side surface. The fiber collection tool of the present Example did not have any depressions on the surface thereof. For the agent having a film-releasing action, talc (product name "SI-Talc JA-46R" from Miyoshi Kasei, Inc.) was used. This agent was applied to the entire fiber collection tool before forming the film F.

Example 2-4

A film F was formed and the film was transferred onto the user's cheek as in Example 2-3, except that, before transferring the film F, an agent for increasing adhesiveness between the object and the film F was applied to the user's cheek. Cosmetic A was used for the agent for increasing adhesiveness between the object and the film F. The composition of Cosmetic A is shown in Table 2 below. The table also shows details (mass %) of the components shown in Table 2.

TABLE 2

| Cosmetic A | | |
| --- | --- | --- |
| Glycerin | 86% Glycerin V, Kao Corporation | 15% |
| Dimethicone | Silicone KF-96A-10CS (-G), Shin-Etsu Chemical Co., Ltd. | 5% |
| BG | 1,3-Butylene glycol-P, KH Neochem Co., Ltd. | 5% |
| Neopentyl glycol dicaprate | Estemol N-01, Nisshin Oillio Group, Ltd. | 5% |
| Cetyl-PGhydroxyethyl palmitamide | Sphingolipid E, Kao Corporation | 2% |
| Glyceryl behenate | Sunsoft No. 8100-CK, Taiyo Kagaku Co., Ltd. | 1% |
| Cetanol | Cetyl Alcohol NX, Kokyu Alcohol Kogyo Co., Ltd. | 1% |
| Stearoyl glutamate | Amisoft HA-P, Ajinomoto Co., Inc. | 1% |
| Water | | Balance |

Example 2-5

A film F was formed and the film was transferred onto the user's cheek as in Example 2-1, except that, before transferring the film F, Cosmetic A was applied to the user's cheek.

Example 2-6

A film F was formed and the film was transferred onto the user's cheek as in Example 2-5, except that the film F was transferred onto a test desk instead of the user's cheek.

Example 2-7

A film F was formed and the film was transferred onto the user's cheek as in Example 2-3, except that no agent having a film-releasing action was applied to the fiber collection tool 1.

Example 2-8

A film F was formed and the film was transferred onto the user's cheek as in Example 2-4, except that, before transferring the film F, Cosmetic B was applied to the user's cheek. Cosmetic B is an agent for increasing adhesiveness between an object and the film F; while Cosmetic A is a moisturizer-like liquid agent, Cosmetic B is a toner-like liquid agent and thus has less adhesiveness than Cosmetic A. The composition of Cosmetic B is shown in Table 3 below. The table also shows details (mass %) of the components shown in Table 3.

TABLE 3

| | Cosmetic B | |
|---|---|---|
| Glycerin | 86% Glycerin V, Kao Corporation | 15% |
| BG | 1,3-Butylene glycol-P, KH Neochem Co., Ltd. | 5% |
| Water | | Balance |

Evaluation of Transferring Properties:

A test was repeated five times, wherein a film F formed on a collection surface of a fiber collection tool was pressed against a transfer-target object to see whether the film F could be transferred or not. Then, based on the number of times that transferring of the entire film F onto the transfer-target object succeeded, the transferring properties were evaluated according to the following criteria. The evaluation results are shown in Table 4.

Criteria for Evaluating Transferring Properties:

A: Transferring succeeded four or more times
B: Transferring succeeded two to three times.
C: Transferring succeeded once.
D: Transferring succeeded zero times.

Evaluation of Finish:

Films for which transferring succeeded in the aforementioned Evaluation of Transferring Properties were observed with the eyes, to evaluate their appearance. Films that were transferred in their entirety and that had no unnatural appearance earned 3 points, whereas films that were partially transferred earned 2 points. For films for which transferring succeeded two or more times, the arithmetic mean value of the evaluation score (points) of each film was calculated. Then, the finish was evaluated according to the following criteria. The evaluation results are shown in Table 4.

Criteria for Evaluating Finish:

A: Evaluation score was from 2.8 to 3 points.
B: Evaluation score was from 2.3 to 2.7 points.
C: Evaluation score was from 2.0 to 2.2 points.

Evaluation of Convenience:

The convenience/easiness of the transferring process was evaluated according to the following criteria, based on the number of steps in the series of processes from formation of the film F using the fiber collection tool 1 to transferring of the film F onto a transfer-target object.

Depending on the Examples, the process not only included a film formation step for forming the film F using the fiber collection tool 1 and a transferring step for pressing the fiber collection tool against a transfer-target object and transferring the film F onto the object, but also included a step for applying, to the fiber collection tool, an agent having a film-releasing action, or a step for applying, to the transfer-target object, an agent for increasing adhesiveness between the object and the film F. The evaluation results are shown in Table 4.

Criteria for Evaluating Convenience:

A: There were 2 steps or less.
B: There were 3 steps or more.

TABLE 4

| | | Example 2-1 | Example 2-2 | Example 2-3 | Example 2-4 | Example 2-5 | Example 2-6 | Example 2-7 | Example 2-8 |
|---|---|---|---|---|---|---|---|---|---|
| Fiber collection tool | Surface depressions | Yes | No | No | No | Yes | Yes | No | No |
| | Napped section | No | Yes | No | No | No | No | No | No |
| | Agent having action of releasing film | No | No | Yes | No | No | No | No | No |
| | Object | Skin | Skin | Skin | Skin | Skin | Non-skin | Skin | Skin |
| | Agent for increasing adhesiveness between object and film | No | No | No | Cosmetic A | Cosmetic A | Cosmetic A | No | Cosmetic B |
| | Evaluation of transferring properties | A | A | A | B | A | A | C | C |
| | Evaluation of finish | B | B | A | C | A | C | C | C |
| | Evaluation of convenience | A | A | B | B | B | B | A | B |

As shown in Table 4, in all the Examples, it was possible to transfer the film F onto the transfer-target object. Particularly, the results of Examples 2-1, 2-2, 2-5, and 2-6 show that, in cases of using fiber collection tools having depressions or napped sections on the surface thereof, the number of times that transferring of the film F succeeded was large, and excellent transferring properties and finish were achieved.

A comparison between Example 2-1 and Example 2-5 shows that, for fiber collection tools having depressions on the surface thereof, it is effective to apply, to the object's surface, an agent for increasing adhesiveness between the object and the film in advance.

The results of Examples 2-3, 2-4, 2-7, and 2-8 show that, for fiber collection tools that do not have depressions on the surface thereof, it is effective to apply an agent having a film-releasing action to the fiber collection tool's surface, or apply in advance, to the object's surface, an agent for increasing adhesiveness between the object and the film Further, the results show that all the Examples were able to transfer the film in a few steps and had excellent convenience.

INDUSTRIAL APPLICABILITY

The present invention provides a fiber deposit production method which enables electro spinning of fiber to be performed in a hand-held state and offers excellent fiber spinnability.

The present invention also provides a film production method and a film attachment method which enable a user to produce a desired film by himself/herself and which are less limited in terms of areas where the film can be attached.

The invention claimed is:

1. A method for producing a fiber deposit, the method comprising:
   collecting a fiber with a fiber collection tool, the fiber being spun by a user by performing electrospinning using an electrospinning device; and
   producing a deposit of the fiber on a surface of the fiber collection tool,
   wherein:
   the fiber collection tool includes, in its interior, an electroconductive section, and
   the electrospinning is performed in in a state where:
   the user holds the fiber collection tool with a hand; or
   the user holds an electric conductor by a hand, and the electric conductor is in contact with the fiber collection tool.

2. A method for producing a fiber deposit, comprising:
   collecting a fiber with a fiber collection tool, the fiber being spun by a user by performing electrospinning using an electrospinning device; and
   producing a deposit of the fiber on a surface of the fiber collection tool,
   wherein:
   the fiber collection tool includes, in its interior, an electroconductive section, and
   the electroconductive section of the fiber collection tool is made from a material deformable by external force applied by the user's grip.

3. The method for producing a fiber deposit according to claim 1, wherein the electrospinning is performed in a state where the user holds the electrospinning device with one hand and holds the fiber collection tool with the other hand, and
   wherein an electrical conduction path passing through the user's body is formed between the electrospinning device and the fiber collection tool.

4. The method for producing a fiber deposit according to claim 1, wherein the electrospinning is performed in a state where the user holds the electrospinning device with one hand and holds an electric conductor with the other hand with the electric conductor in contact with the fiber collection tool, and
   wherein an electrical conduction path passing through the user's body and the electric conductor is formed between the electrospinning device and the fiber collection tool.

5. The method for producing a fiber deposit according to claim 1, wherein the fiber collection tool has a volume electrical resistivity of $10^{10}$ Ω·cm or less.

6. The method for producing a fiber deposit according to claim 1, wherein:
   the fiber collection tool further includes a surface section outside the electroconductive section; and
   the surface section has a surface electrical resistivity of greater than $10^{11}$ Ω/cm$^2$.

7. The method for producing a fiber deposit according to claim 1, wherein:
   the fiber collection tool further includes a surface section outside the electroconductive section; and
   the surface section has elasticity.

8. A method for producing a film on a surface of an object, the film comprising a fiber deposit, the method comprising:
   forming a film including a deposit of the fiber on a surface of a fiber collection tool, the forming being performed by a user by performing electrospinning using an electrospinning device; and
   pressing the fiber collection tool, which has the film formed thereon, against a surface of an object and transferring the film onto the surface of the object, to form the film including the fiber deposit on the surface of the object,
   wherein:
   the fiber collection tool includes, in its interior, an electroconductive section, and the electrospinning is performed in in a state where:
   the user holds the fiber collection tool with a hand; or
   the user holds an electric conductor by a hand, and the electric conductor is in contact with the fiber collection tool.

9. The method for producing a film according to claim 8, wherein:
   one or both of the electrospinning device and the fiber collection tool has/have a size holdable by the user's hand;
   the user collects the fiber with the fiber collection tool, and forms the film including the fiber deposit on the surface of the fiber collection tool; and
   the user presses the fiber collection tool, having the film formed thereon, against the surface of the object.

10. The method for producing a film according to claim 8, wherein the fiber collection tool has, in the surface thereof, one or a plurality of depressions.

11. The method for producing a film according to claim 8, wherein the fiber collection tool has, on the surface thereof, a section including napped fiber.

12. The method for producing a film according to claim 8, wherein the fiber collection tool has, on the surface thereof, an agent having an action of releasing the film.

13. The method for producing a film according to claim 8, the method further comprising:
    applying in advance, to the surface of the object, an agent for increasing adhesiveness between the object and the film, and in this state, pressing the fiber collection tool, having the film formed thereon, against the surface of the object.

14. The method for producing a film according to claim 8, wherein the film formed on the surface of the fiber collection tool has a higher adhesiveness to the object than the adhesiveness to the fiber collection tool.

* * * * *